(12) United States Patent
Yun et al.

(10) Patent No.: US 10,304,580 B2
(45) Date of Patent: May 28, 2019

(54) TALBOT X-RAY MICROSCOPE

(71) Applicant: Sigray, Inc., Concord, CA (US)

(72) Inventors: Wenbing Yun, Walnut Creek, CA (US); David Vine, Berkeley, CA (US); Sylvia Jia Yun Lewis, San Francisco, CA (US); Janos Kirz, Berkeley, CA (US); Srivatsan Seshadri, Pleasanton, CA (US)

(73) Assignee: Sigray, Inc., Concord, CA (US)

( * ) Notice: Subject to any disclaimer, the term of this patent is extended or adjusted under 35 U.S.C. 154(b) by 0 days.

(21) Appl. No.: 15/954,380

(22) Filed: Apr. 16, 2018

(65) Prior Publication Data
US 2018/0261350 A1 Sep. 13, 2018

Related U.S. Application Data

(63) Continuation-in-part of application No. 14/712,917, filed on May 15, 2015, now Pat. No. 9,874,531.
(Continued)

(51) Int. Cl.
*G01N 23/00* (2006.01)
*G21K 1/02* (2006.01)
(Continued)

(52) U.S. Cl.
CPC .......... *G21K 1/025* (2013.01); *G01N 23/083* (2013.01); *G21K 7/00* (2013.01); *G01N 2223/204* (2013.01)

(58) Field of Classification Search
CPC .............................. G21K 7/00; G21K 2207/00
See application file for complete search history.

(56) References Cited

U.S. PATENT DOCUMENTS 1,203,495 A 10/1916 Coolidge
1,211,092 A 1/1917 Coolidge
(Continued)

FOREIGN PATENT DOCUMENTS

CN 102124537 A 7/2011
EP 0432568 6/1991
(Continued)

OTHER PUBLICATIONS

"Diamond," Section 10.4.2 of Zorman et al., "Material Aspects of Micro-Nanoelectromechanical Systems," Chapter 10 of Springer Handbook of Nanotechnology, 2nd ed., Barat Bushan, ed. (Springer Science + Business Media, Inc., New York, 2007), pp. 312-314.
(Continued)

*Primary Examiner* — Dani Fox
(74) *Attorney, Agent, or Firm* — Knobbe, Martens, Olson & Bear, LLP

(57) ABSTRACT

Systems for x-ray microscopy using an array of microbeams having a micro- or nano-scale beam intensity profile to provide selective illumination of micro- or nano-scale regions of an object. An array detector is positioned such that each pixel of the detector only detects x-rays corresponding to a single micro-or nano-beam. This allows the signal arising from each x-ray detector pixel to be identified with the specific, limited micro- or nano-scale region illuminated, allowing sampled transmission image of the object at a micro- or nano-scale to be generated while using a detector with pixels having a larger size and scale. Detectors with higher quantum efficiency may therefore be used, since the lateral resolution is provided solely by the dimensions of the micro- or nano-beams. The micro- or nano-scale beams may be generated using a arrayed x-ray source and a set of Talbot interference fringes.

21 Claims, 17 Drawing Sheets

Related U.S. Application Data which is a continuation-in-part of application No. 14/700,137, filed on Apr. 29, 2015, now Pat. No. 9,719,947, which is a continuation-in-part of application No. 14/527,523, filed on Oct. 29, 2014, now abandoned.

(60) Provisional application No. 62/485,916, filed on Apr. 15, 2017, provisional application No. 61/981,098, filed on Apr. 17, 2014, provisional application No. 61/901,361, filed on Nov. 7, 2013, provisional application No. 61/898,019, filed on Oct. 31, 2013, provisional application No. 61/993,792, filed on May 15, 2014.

(51) Int. Cl.
*G01N 23/083* (2018.01)
*G21K 7/00* (2006.01)

(56) References Cited

U.S. PATENT DOCUMENTS

| | | |
|---|---|---|
| 1,215,116 A | 2/1917 | Coolidge |
| 1,328,495 A | 1/1920 | Coolidge |
| 1,355,126 A | 10/1920 | Coolidge |
| 1,790,073 A | 1/1931 | Pohl |
| 1,917,099 A | 7/1933 | Coolidge |
| 1,946,312 A | 2/1934 | Coolidge |
| 2,926,270 A | 2/1960 | Zunick |
| 3,795,832 A | 3/1974 | Holland |
| 4,227,112 A | 10/1980 | Waugh et al. |
| 4,266,138 A | 5/1981 | Nelson et al. |
| 4,426,718 A | 1/1984 | Hayashi |
| 4,523,327 A | 6/1985 | Eversole |
| 4,573,186 A | 2/1986 | Reinhold |
| 4,807,268 A | 2/1989 | Wittrey |
| 4,940,319 A | 7/1990 | Ueda et al. |
| 4,951,304 A | 8/1990 | Piestrup et al. |
| 4,972,449 A | 11/1990 | Upadhya et al. |
| 5,001,737 A | 3/1991 | Lewis et al. |
| 5,008,918 A | 4/1991 | Lee et al. |
| 5,132,997 A | 7/1992 | Kojima |
| 5,148,462 A | 9/1992 | Spitsyn et al. |
| 5,173,928 A | 12/1992 | Momose et al. |
| 5,249,216 A | 9/1993 | Ohsugi et al. |
| 5,276,724 A | 1/1994 | Kumasaka et al. |
| 5,602,899 A | 2/1997 | Larson |
| 5,604,782 A | 2/1997 | Cash, Jr. |
| 5,629,969 A | 5/1997 | Koshishiba |
| 5,657,365 A | 8/1997 | Yamamoto et al. |
| 5,682,415 A | 10/1997 | O'Hara |
| 5,715,291 A | 2/1998 | Momose |
| 5,729,583 A | 3/1998 | Tang et al. |
| 5,768,339 A | 6/1998 | O'Hara |
| 5,772,903 A | 6/1998 | Hirsch |
| 5,778,039 A | 7/1998 | Hossain |
| 5,812,629 A | 9/1998 | Clauser |
| 5,825,848 A | 10/1998 | Virshup et al. |
| 5,832,052 A | 11/1998 | Hirose et al. |
| 5,857,008 A | 1/1999 | Reinhold |
| 5,878,110 A | 3/1999 | Yamamoto et al. |
| 5,881,126 A | 3/1999 | Momose |
| 5,912,940 A | 6/1999 | O'Hara |
| 5,930,325 A | 7/1999 | Momose |
| 6,108,397 A | 8/2000 | Cash, Jr. |
| 6,108,398 A | 8/2000 | Mazor et al. |
| 6,125,167 A | 9/2000 | Morgan |
| 6,278,764 B1 | 8/2001 | Barbee, Jr. et al. |
| 6,359,964 B1 | 3/2002 | Kogan |
| 6,377,660 B1 | 4/2002 | Ukita et al. |
| 6,381,303 B1 | 4/2002 | Vu et al. |
| 6,389,100 B1 | 5/2002 | Verman et al. |
| 6,430,254 B2 | 8/2002 | Wilkins |
| 6,442,231 B1 | 8/2002 | O'Hara |
| 6,456,688 B1 | 9/2002 | Taguchi et al. |
| 6,463,123 B1 | 10/2002 | Korenev |
| 6,487,272 B1 | 11/2002 | Kutsuzawa |
| 6,504,902 B2 | 1/2003 | Iwasaki et al. |
| 6,507,388 B2 | 1/2003 | Burghoorn |
| 6,553,096 B1 | 4/2003 | Zhou et al. |
| 6,560,313 B1 | 5/2003 | Harding et al. |
| 6,560,315 B1 | 5/2003 | Price et al. |
| 6,707,883 B1 | 3/2004 | Tiearney et al. |
| 6,711,234 B1 | 3/2004 | Loxley et al. |
| 6,811,612 B2 | 11/2004 | Gruen et al. |
| 6,815,363 B2 | 11/2004 | Yun et al. |
| 6,829,327 B1 | 12/2004 | Chen |
| 6,847,699 B2 | 1/2005 | Rigali et al. |
| 6,850,598 B1 | 2/2005 | Fryda et al. |
| 6,870,172 B1 | 3/2005 | Mankos et al. |
| 6,885,503 B2 | 4/2005 | Yun et al. |
| 6,914,723 B2 | 7/2005 | Yun et al. |
| 6,917,472 B1 | 7/2005 | Yun et al. |
| 6,947,522 B2 | 9/2005 | Wilson et al. |
| 6,975,703 B2 | 12/2005 | Wilson et al. |
| 7,003,077 B2 | 2/2006 | Jen et al. |
| 7,006,596 B1 | 2/2006 | Janik |
| 7,015,467 B2 | 3/2006 | Maldonado et al. |
| 7,023,955 B2 | 4/2006 | Chen et al. |
| 7,057,187 B1 | 6/2006 | Yun et al. |
| 7,079,625 B2 | 7/2006 | Lenz |
| 7,095,822 B1 | 8/2006 | Yun |
| 7,110,503 B1 | 9/2006 | Kumakhov |
| 7,119,953 B2 | 10/2006 | Yun et al. |
| 7,130,375 B1 | 10/2006 | Yun et al. |
| 7,170,969 B1 | 1/2007 | Yun et al. |
| 7,180,979 B2 | 2/2007 | Momose |
| 7,180,981 B2 | 2/2007 | Wang |
| 7,183,547 B2 | 2/2007 | Yun et al. |
| 7,215,736 B1 | 5/2007 | Wang et al. |
| 7,215,741 B2 | 5/2007 | Ukita et al. |
| 7,218,700 B2 | 5/2007 | Huber et al. |
| 7,218,703 B2 | 5/2007 | Yada et al. |
| 7,221,731 B2 | 5/2007 | Yada et al. |
| 7,245,696 B2 | 7/2007 | Yun et al. |
| 7,268,945 B2 | 9/2007 | Yun et al. |
| 7,286,640 B2 | 10/2007 | Yun et al. |
| 7,297,959 B2 | 11/2007 | Yun et al. |
| 7,298,826 B2 | 11/2007 | Inazuru |
| 7,330,533 B2 | 2/2008 | Sampayon |
| 7,346,148 B2 | 3/2008 | Ukita |
| 7,346,204 B2 | 3/2008 | Ito |
| 7,359,487 B1 | 4/2008 | Newcome |
| 7,365,909 B2 | 4/2008 | Yun et al. |
| 7,365,918 B1 | 4/2008 | Yun et al. |
| 7,382,864 B2 | 6/2008 | Hebert et al. |
| 7,388,942 B2 | 6/2008 | Wang et al. |
| 7,394,890 B1 | 7/2008 | Wang et al. |
| 7,400,704 B1 | 7/2008 | Yun et al. |
| 7,406,151 B1 | 7/2008 | Yun |
| 7,412,024 B1 | 8/2008 | Yun et al. |
| 7,412,030 B1 | 8/2008 | O'Hara |
| 7,412,131 B2 | 8/2008 | Lee et al. |
| 7,414,787 B2 | 8/2008 | Yun et al. |
| 7,433,444 B2 | 10/2008 | Baumann |
| 7,443,953 B1 | 10/2008 | Yun et al. |
| 7,453,981 B2 | 11/2008 | Baumann |
| 7,463,712 B2 | 12/2008 | Zhu et al. |
| 7,486,770 B2 | 2/2009 | Baumann |
| 7,492,871 B2 | 2/2009 | Popescu |
| 7,499,521 B2 | 3/2009 | Wang et al. |
| 7,515,684 B2 | 4/2009 | Gibson et al. |
| 7,522,698 B2 | 4/2009 | Popescu |
| 7,522,707 B2 | 4/2009 | Steinlage et al. |
| 7,522,708 B2 | 4/2009 | Heismann |
| 7,529,343 B2 | 5/2009 | Safai et al. |
| 7,532,704 B2 | 5/2009 | Hempel |
| 7,551,719 B2 | 6/2009 | Yokhin et al. |
| 7,551,722 B2 | 6/2009 | Ohshima et al. |
| 7,561,662 B2 | 7/2009 | Wang et al. |
| 7,564,941 B2 | 7/2009 | Baumann |
| 7,583,789 B1 | 9/2009 | Macdonald et al. |
| 7,601,399 B2 | 10/2009 | Barnola et al. |

(56) References Cited

U.S. PATENT DOCUMENTS

| | | |
|---|---|---|
| 7,639,786 B2 | 12/2009 | Baumann |
| 7,646,843 B2 | 1/2010 | Popescu et al. |
| 7,672,433 B2 | 3/2010 | Zhong et al. |
| 7,680,243 B2 | 3/2010 | Yokhin et al. |
| 7,787,588 B1 | 8/2010 | Yun et al. |
| 7,796,725 B1 | 9/2010 | Yun et al. |
| 7,796,726 B1 | 9/2010 | Gendreau et al. |
| 7,800,072 B2 | 9/2010 | Yun et al. |
| 7,813,475 B1 | 10/2010 | Wu et al. |
| 7,817,777 B2 | 10/2010 | Baumann et al. |
| 7,864,426 B2 | 1/2011 | Yun et al. |
| 7,864,922 B2 | 1/2011 | Kawabe |
| 7,873,146 B2 | 1/2011 | Okunuki et al. |
| 7,876,883 B2 | 1/2011 | O'Hara |
| 7,889,838 B2 | 2/2011 | David et al. |
| 7,889,844 B2 | 2/2011 | Okunuki et al. |
| 7,914,693 B2 | 3/2011 | Jeong et al. |
| 7,920,673 B2 | 4/2011 | Lanza et al. |
| 7,920,676 B2 | 4/2011 | Yun et al. |
| 7,924,973 B2 | 4/2011 | Kottler et al. |
| 7,929,667 B1 | 4/2011 | Zhuang et al. |
| 7,945,018 B2 | 5/2011 | Heismann |
| 7,949,092 B2 | 5/2011 | Brons |
| 7,949,095 B2 | 5/2011 | Ning |
| 7,974,379 B1 | 7/2011 | Case et al. |
| 7,983,381 B2 | 7/2011 | David et al. |
| 7,991,120 B2 | 8/2011 | Okunuki et al. |
| 8,005,185 B2 | 8/2011 | Popescu |
| 8,009,796 B2 | 8/2011 | Popescu |
| 8,041,004 B2 | 10/2011 | David |
| 8,036,341 B2 | 11/2011 | Lee |
| 8,058,621 B2 | 11/2011 | Kommareddy et al. |
| 8,068,579 B1 | 11/2011 | Yun et al. |
| 8,073,099 B2 | 12/2011 | Niu et al. |
| 8,094,784 B2 | 1/2012 | Morton |
| 8,139,716 B2 | 3/2012 | Okunuki et al. |
| 8,184,771 B2 | 5/2012 | Murakoshi |
| 8,208,602 B2 | 6/2012 | Lee et al. |
| 8,208,603 B2 | 6/2012 | Sato |
| 8,243,879 B2 | 8/2012 | Itoh et al. |
| 8,243,884 B2 | 8/2012 | Rödhammer et al. |
| 8,280,000 B2 | 10/2012 | Takahashi |
| 8,306,183 B2 | 11/2012 | Koehler |
| 8,306,184 B2 | 11/2012 | Chang et al. |
| 8,351,569 B2 | 1/2013 | Baker |
| 8,351,570 B2 | 1/2013 | Nakamura |
| 8,353,628 B1 | 1/2013 | Yun et al. |
| 8,360,640 B2 | 1/2013 | Reinhold |
| 8,374,309 B2 | 2/2013 | Donath |
| 8,406,378 B2 | 3/2013 | Wang et al. |
| 8,416,920 B2 | 4/2013 | Okumura et al. |
| 8,422,633 B2 | 4/2013 | Lantz et al. |
| 8,451,975 B2 | 5/2013 | Tada |
| 8,422,637 B2 | 6/2013 | Okunuki et al. |
| 8,509,386 B2 | 8/2013 | Lee et al. |
| 8,520,803 B2 | 8/2013 | Behling |
| 8,526,575 B1 | 9/2013 | Yun et al. |
| 8,532,257 B2 | 9/2013 | Mukaide et al. |
| 8,553,843 B2 | 10/2013 | Drory |
| 8,559,597 B2 | 10/2013 | Chen et al. |
| 8,565,371 B2 | 10/2013 | Bredno |
| 8,576,983 B2 | 11/2013 | Baeumer |
| 8,591,108 B2 | 11/2013 | Tada |
| 8,602,648 B1 | 12/2013 | Jacobsen et al. |
| 8,632,247 B2 | 1/2014 | Ishii |
| 8,666,024 B2 | 3/2014 | Okunuki et al. |
| 8,666,025 B2 | 3/2014 | Klausz |
| 8,699,667 B2 | 4/2014 | Steinlage et al. |
| 8,735,844 B1 | 5/2014 | Khaykovich et al. |
| 8,737,565 B1 | 5/2014 | Lyon et al. |
| 8,744,048 B2 | 6/2014 | Lee et al. |
| 8,755,487 B2 | 6/2014 | Kaneko |
| 8,767,915 B2 | 7/2014 | Stutman |
| 8,767,916 B2 | 7/2014 | Hashimoto |
| 8,781,069 B2 | 7/2014 | Murakoshi |
| 8,824,629 B2 | 9/2014 | Ishii |
| 8,831,174 B2 | 9/2014 | Kohara |
| 8,831,175 B2 | 9/2014 | Silver et al. |
| 8,831,179 B2 | 9/2014 | Adler et al. |
| 8,855,265 B2 | 10/2014 | Engel |
| 8,861,682 B2 | 10/2014 | Okunuki et al. |
| 8,903,042 B2 | 12/2014 | Ishii |
| 8,995,622 B2 | 3/2015 | Adler et al. |
| 9,001,967 B2 | 4/2015 | Baturin |
| 9,008,278 B2 | 4/2015 | Lee et al. |
| 9,016,943 B2 | 4/2015 | Jacobsen et al. |
| 9,020,101 B2 | 4/2015 | Omote et al. |
| 9,129,715 B2 | 9/2015 | Adler et al. |
| 9,329,141 B2 | 5/2016 | Stutman |
| 9,357,975 B2 | 6/2016 | Baturin |
| 9,390,881 B2 | 7/2016 | Yun et al. |
| 9,439,613 B2 | 9/2016 | Stutman |
| 9,448,190 B2 | 9/2016 | Yun et al. |
| 9,449,781 B2 | 9/2016 | Yun et al. |
| 9,543,109 B2 | 1/2017 | Yun et al. |
| 9,570,265 B1 | 2/2017 | Yun et al. |
| 9,594,036 B2 | 3/2017 | Yun et al. |
| 9,632,040 B2 | 4/2017 | Stutman |
| 9,719,947 B2 | 8/2017 | Yun et al. |
| 9,823,203 B2 | 11/2017 | Yun et al. |
| 9,874,531 B2 | 1/2018 | Yun et al. |
| 9,939,392 B2 | 4/2018 | Wen |
| 2001/0006413 A1 | 7/2001 | Burghoorn |
| 2002/0085676 A1 | 7/2002 | Snyder |
| 2003/0142790 A1 | 1/2003 | Zhou et al. |
| 2003/0223536 A1 | 12/2003 | Yun et al. |
| 2004/0120463 A1 | 6/2004 | Wilson et al. |
| 2004/0140432 A1 | 7/2004 | Maldonado et al. |
| 2005/0074094 A1 | 4/2005 | Jen et al. |
| 2005/0123097 A1 | 6/2005 | Wang |
| 2005/0163284 A1 | 7/2005 | Inazuru |
| 2005/0282300 A1 | 12/2005 | Yun et al. |
| 2006/0045234 A1* | 3/2006 | Pelc .................. A61B 6/032 378/9 |
| 2006/0062350 A1 | 3/2006 | Yokhin |
| 2007/0030959 A1 | 2/2007 | Ritter |
| 2007/0071174 A1 | 3/2007 | Hebert et al. |
| 2007/0108387 A1 | 5/2007 | Yun et al. |
| 2007/0110217 A1 | 5/2007 | Ukita |
| 2007/0183563 A1 | 8/2007 | Baumann |
| 2007/0183579 A1 | 8/2007 | Baumann et al. |
| 2007/0189449 A1 | 8/2007 | Baumann |
| 2007/0248215 A1 | 10/2007 | Ohshima et al. |
| 2008/0084966 A1 | 4/2008 | Aoki et al. |
| 2008/0089484 A1 | 4/2008 | Reinhold |
| 2008/0094694 A1 | 4/2008 | Yun et al. |
| 2008/0159707 A1 | 7/2008 | Lee et al. |
| 2008/0165355 A1 | 7/2008 | Yasui et al. |
| 2008/0170662 A1 | 7/2008 | Reinhold |
| 2008/0170668 A1 | 7/2008 | Kruit et al. |
| 2008/0181363 A1 | 7/2008 | Fenter et al. |
| 2008/0240344 A1 | 10/2008 | Reinhold |
| 2008/0273662 A1 | 11/2008 | Yun |
| 2009/0052619 A1* | 2/2009 | Endoh .................. G01N 23/04 378/43 |
| 2009/0092227 A1 | 4/2009 | David |
| 2009/0154640 A1 | 6/2009 | Baumann et al. |
| 2009/0316860 A1 | 12/2009 | Okunuki et al. |
| 2010/0012845 A1 | 1/2010 | Baeumer et al. |
| 2010/0027739 A1 | 2/2010 | Lantz et al. |
| 2010/0040202 A1 | 2/2010 | Lee |
| 2010/0046702 A1 | 2/2010 | Chen et al. |
| 2010/0061508 A1 | 3/2010 | Takahashi |
| 2010/0091947 A1 | 4/2010 | Niu |
| 2010/0141151 A1 | 6/2010 | Reinhold |
| 2010/0246765 A1 | 9/2010 | Murakoshi |
| 2010/0260315 A1 | 10/2010 | Sato et al. |
| 2010/0272239 A1 | 10/2010 | Lantz et al. |
| 2010/0284513 A1 | 11/2010 | Kawabe |
| 2011/0026680 A1 | 2/2011 | Sato |
| 2011/0038455 A1 | 2/2011 | Silver et al. |
| 2011/0058655 A1 | 3/2011 | Okumura et al. |
| 2011/0064191 A1 | 3/2011 | Toth et al. |
| 2011/0085644 A1 | 4/2011 | Verman |

(56) References Cited

U.S. PATENT DOCUMENTS

| | | |
|---|---|---|
| 2011/0135066 A1 | 6/2011 | Behling |
| 2011/0142204 A1 | 6/2011 | Zou et al. |
| 2011/0235781 A1 | 9/2011 | Aoki et al. |
| 2011/0243302 A1 | 10/2011 | Murakoshi |
| 2011/0268252 A1 | 11/2011 | Ozawa et al. |
| 2012/0041679 A1 | 2/2012 | Stampanoni |
| 2012/0057669 A1 | 3/2012 | Vogtmeier et al. |
| 2012/0163547 A1 | 6/2012 | Lee et al. |
| 2012/0163554 A1 | 6/2012 | Tada |
| 2012/0224670 A1 | 9/2012 | Kiyohara et al. |
| 2012/0228475 A1 | 9/2012 | Pang et al. |
| 2012/0269323 A1 | 10/2012 | Adler et al. |
| 2012/0269324 A1 | 10/2012 | Adler |
| 2012/0269325 A1 | 10/2012 | Adler et al. |
| 2012/0269326 A1 | 10/2012 | Adler et al. |
| 2012/0294420 A1 | 11/2012 | Nagai |
| 2013/0011040 A1 | 1/2013 | Kido et al. |
| 2013/0032727 A1 | 2/2013 | Kondoe |
| 2013/0039460 A1 | 2/2013 | Levy |
| 2013/0108012 A1 | 5/2013 | Sato |
| 2013/0108022 A1 | 5/2013 | Kugland et al. |
| 2013/0195246 A1 | 8/2013 | Tamura et al. |
| 2013/0223594 A1 | 8/2013 | Sprong et al. |
| 2013/0259207 A1 | 10/2013 | Omote et al. |
| 2013/0279651 A1 | 10/2013 | Yokoyama |
| 2013/0308112 A1 | 11/2013 | Clube et al. |
| 2013/0308754 A1 | 11/2013 | Yamazaki et al. |
| 2014/0023973 A1 | 1/2014 | Marconi et al. |
| 2014/0037052 A1 | 2/2014 | Adler |
| 2014/0064445 A1 | 3/2014 | Adler |
| 2014/0072104 A1 | 3/2014 | Jacobsen et al. |
| 2014/0079188 A1 | 3/2014 | Hesselink et al. |
| 2014/0105363 A1 | 4/2014 | Chen et al. |
| 2014/0146945 A1 | 5/2014 | Fredenberg et al. |
| 2014/0153692 A1 | 6/2014 | Larkin et al. |
| 2014/0177800 A1 | 6/2014 | Sato et al. |
| 2014/0185778 A1 | 7/2014 | Lee et al. |
| 2014/0205057 A1 | 7/2014 | Koehler et al. |
| 2014/0211919 A1 | 7/2014 | Ogura et al. |
| 2014/0226785 A1 | 8/2014 | Stutman et al. |
| 2014/0241493 A1 | 8/2014 | Yokoyama |
| 2014/0270060 A1 | 9/2014 | Date et al. |
| 2014/0369469 A1 | 12/2014 | Ogura et al. |
| 2015/0030126 A1 | 1/2015 | Radicke |
| 2015/0030127 A1 | 1/2015 | Aoki et al. |
| 2015/0043713 A1 | 2/2015 | Chen |
| 2015/0049860 A1 | 2/2015 | Das |
| 2015/0055743 A1 | 2/2015 | Vedantham et al. |
| 2015/0055745 A1 | 2/2015 | Holzner et al. |
| 2015/0092924 A1 | 4/2015 | Yun et al. |
| 2015/0110252 A1 | 4/2015 | Yun et al. |
| 2015/0117599 A1 | 4/2015 | Yun et al. |
| 2015/0194287 A1 | 7/2015 | Yun et al. |
| 2015/0243397 A1 | 8/2015 | Yun et al. |
| 2015/0247811 A1 | 9/2015 | Yun et al. |
| 2015/0260663 A1 | 9/2015 | Yun et al. |
| 2015/0357069 A1 | 12/2015 | Yun et al. |
| 2016/0064175 A1 | 3/2016 | Yun et al. |
| 2016/0066870 A1 | 3/2016 | Yun et al. |
| 2016/0106387 A1 | 4/2016 | Kahn |
| 2016/0178540 A1 | 6/2016 | Yun et al. |
| 2016/0268094 A1 | 9/2016 | Yun et al. |
| 2016/0320320 A1 | 11/2016 | Yun et al. |
| 2016/0351370 A1 | 12/2016 | Yun et al. |
| 2017/0047191 A1 | 2/2017 | Yun et al. |
| 2017/0052128 A1 | 2/2017 | Yun et al. |
| 2017/0162288 A1 | 6/2017 | Yun et al. |
| 2017/0162359 A1 | 6/2017 | Tang et al. |
| 2017/0227476 A1 | 8/2017 | Zhang et al. |
| 2017/0234811 A1 | 8/2017 | Zhang et al. |
| 2017/0261442 A1 | 9/2017 | Yun et al. |
| 2017/0336334 A1 | 11/2017 | Yun et al. |
| 2018/0144901 A1 | 5/2018 | Yun et al. |
| 2018/0261352 A1 | 9/2018 | Matsuyama et al. |
| 2018/0306734 A1 | 10/2018 | Morimoto et al. |

FOREIGN PATENT DOCUMENTS

| | | |
|---|---|---|
| EP | 0751533 | 1/1997 |
| EP | 1028451 | 8/2000 |
| FR | 2548447 | 1/1985 |
| JP | H06-188092 | 7/1994 |
| JP | H07-056000 | 3/1995 |
| JP | H08-184572 | 7/1996 |
| JP | 2000-306533 | 11/2000 |
| JP | 2007-218683 | 8/2007 |
| JP | 2007-265981 | 10/2007 |
| JP | 2007-311185 | 11/2007 |
| JP | 2008-200359 | 4/2008 |
| JP | 2008-197495 | 8/2008 |
| JP | 2009-195349 | 3/2009 |
| JP | 2009-212058 | 9/2009 |
| JP | 2010-236986 | 10/2010 |
| JP | 2011-029072 | 2/2011 |
| JP | 2011-218147 | 11/2011 |
| JP | 2012-187341 | 10/2012 |
| JP | 2013-508683 | 3/2013 |
| JP | 2013-157269 | 8/2013 |
| JP | 2013-160637 | 8/2013 |
| JP | 2013-239317 | 11/2013 |
| JP | 2015-002074 | 1/2015 |
| JP | 2015-047306 | 3/2015 |
| JP | 2015-077289 | 4/2015 |
| WO | WO 1995/006952 | 3/1995 |
| WO | WO 1998/011592 | 3/1998 |
| WO | WO 2002/039792 | 5/2002 |
| WO | WO 2003/081631 | 10/2003 |
| WO | WO 2005/109969 | 11/2005 |
| WO | WO 2006/096052 | 9/2006 |
| WO | WO 2007/1125833 | 11/2007 |
| WO | WO 2009/098027 | 8/2009 |
| WO | WO 2009/1104560 | 8/2009 |
| WO | WO 2011/032572 | 3/2011 |
| WO | WO 2012/032950 | 3/2012 |
| WO | WO 2013/004574 | 1/2013 |
| WO | WO 2013/111050 | 8/2013 |
| WO | WO 2013/118593 | 8/2013 |
| WO | WO 2013/160153 | 10/2013 |
| WO | WO 2013/168468 | 11/2013 |
| WO | WO 2014/054497 | 4/2014 |
| WO | WO 2015/016019 | 2/2015 |
| WO | WO 2015/034791 | 3/2015 |
| WO | WO 2015/066333 | 5/2015 |
| WO | WO 2015/084466 | 6/2015 |
| WO | WO 2015/168473 | 11/2015 |
| WO | WO 2015/176023 | 11/2015 |
| WO | WO 2015/187219 | 12/2015 |
| WO | WO 2016/187623 | 11/2016 |
| WO | WO 2017/031740 | 3/2017 |
| WO | WO 2017/204850 | 11/2017 |
| WO | WO 2017/213996 | 12/2017 |
| WO | WO 2018/175570 | 9/2018 |

OTHER PUBLICATIONS

"Element Six CVD Diamond Handbook" (Element Six, Luxembourg, 2015).

"High performance benchtop EDXRF spectrometer with Windows® software," published by: Rigaku Corp., Tokyo, Japan; 2017.

"Monochromatic Doubly Curved Crystal Optics," published by: X-Ray Optical Systems, Inc. (XOS), East Greenbush, NY; 2017.

"Optics and Detectors," Section 4 of XS-Ray Data Booklet, 3rd Ed., A.C. Thompson ed. (Lawrence Berkeley Nat'l Lab, Berkeley, CA, 2009).

"Properties of Solids," Ch. 12 of CRC Handbook of Chemistry and Physics, 90th ed., Devid R. Lide & W.M. "Mickey" Haynes, eds. (CRC Press, Boca Raton, FL, 2009), pp. 12-41-12-46; 12-203-12-212.

"Science and Technology of Future Light Sources", Arthur L. Robinson (LBNL) and Brad Plummer (SLAG), eds. Report Nos. ANL-08/39 / BNL-81895-2008 / LBNL-1090E-2009 / SLAC-R-917 (Lawrence Berkeley Nat'l Lab, Berkeley, CA, Dec. 2008).

(56) References Cited

OTHER PUBLICATIONS

"Series 5000 Packaged X-ray Tubes," Product Technical Data Sheet DS006 Rev. G, X-Ray Technologies Inc. (Oxford Insstruments), Scotts Valley, CA (no date).
"Toward Control of Matter: Energy Science Needs for a New Class of X-Ray Light Sources" (Lawrence Berkeley Nat'l Lab, Berkeley, CA, Sep. 2008).
"X-ray Optics for BES Light Source Facilities," Report of the Basic Energy Sciences Workshop on X-ray Optics for BES Light Source Facilities, D. Mills & H. Padmore, Co-Chairs, (U.S. Dept. of Energy, Office of Science, Potomac, MD, Mar. 2013).
Abullian et al., "Quantitative determination of the lateral density and intermolecular correlation between proteins anchored on the membrane surfaces using grazing incidence small-angle X-ray scattering and grazing incidence X-ray fluorescence," Nov. 28, 2012, The Journal of Chemical Physics, vol. 137, pp. 204907-1 to 204907-8.
Adachi et al., "Development of the 17-inch Direct-Conversion Dynamic Flat-panel X-ray Detector (FPD)," Digital R/F (Shimadzu Corp., 2 pages (no date, published—2004 with product release).
Aharonovich et al., "Diamond Nanophotonics," Adv. Op. Mat'ls vol. 2, Issue 10 (2014).
Als-Nielsen et al., "Phase contrast imaging" Sect. 9.3 of Ch. 9 of "Elements of Modern X-ray Physics, Second Edition" , (John Wiley & Sons Ltd, Chichester, West Sussex, UK, 2011), pp. 318-329.
Als-Nielsen et al., "Photoelectric Absorption," Ch. 7 of "Elements of Modern X-ray Physics, Second Edition," (John Wiley & Sons Ltd, Chichester, West Sussex, UK, 2011).
Als-Nielsen et al., "Refraction and reflection from interfaces," Ch. 3 of "Elements of Modern X-ray Physics, Second Edition," (John Wiley & Sons Ltd., Chichester, West Sussex, UK, 2011), pp. 69-112.
Als-Nielsen et al., "X-rays and their interaction with matter", and "Sources", Ch. 1 & 2 of "Elements of Modern X-ray Physics, Second Edition" (John Wiley & Sons Ltd, Chichester, West Sussex, UK, 2011).
Altapova et al., "Phase contrast laminography based on Talbot interferometry," Opt. Express, vol. 20, No. 6, (2012) pp. 6496-6508.
Ando et al., "Smooth and high-rate reactive ion etching of diamond," Diamond and Related Materials, vol. 11, (2002) pp. 824-827.
Arfelli et al., "Mammography with Synchrotron Radiation: Phase-Detection Techniques," Radiology vol. 215, (2000), pp. 286-293.
Arndt et al., Focusing Mirrors for Use with Microfocus X-ray Tubes, 1998, Journal of Applied Crystallography, vol. 31, pp. 733-741.
Balaic et al., "X-ray optics of tapered capillaries," Appl. Opt. vol. 34 (Nov. 1995) pp. 7263-7272.
Baltes et al., "Coherent and incoherent grating reconstruction," J. Opt. Soc. Am. A vol. 3(8), (1986), pp. 1268-1275.
Barbee Jr., "Multilayers for x-ray optics," Opt. Eng. vol. 25 (Aug. 1986) pp. 898-915.
Baron et al., "A compact optical design for Bragg reflections near backscattering," J. Synchrotron Rad., vol. 8 (2001), pp. 1127-1130.
Bech, "In-vivo dark-field and phase-contrast x-ray imaging," Scientific Reports 3, (2013), Article No. 03209.
Bech, "X-ray imaging with a grating interferometer," University of Copenhagen PhD. Thesis, (May 1, 2009).
Bergamin et al., "Measuring small lattice distortions in Si-crystals by phase-contrast x-ray topography," J. Phys. D: Appl. Phys. vol. 33 (Dec. 31, 2000) pp. 2678-2682.
Bernstorff, "Grazing Incidence Small Angle X-ray Scattering (GISAXS)," Presentation at Advanced School on Synchrotron and Free Electron Laser Sources and their Multidisciplinary Applications, Apr. 2008, Trieste, Italy.
Bilderback et al., "Single Capillaries," Ch. 29 of "Handbook of Optics vol. III, 2nd Ed." (McGraw Hill, New York, 2001).
Birkholz, "Chapter 4: Grazing Incidence Configurations," Thin Film Analysis by X-ray Scattering (Wiley-VCH Verlag GmbH & Co. KGaA, Weinheim, Germany, 2006).
Bjeoumikhov et al., "A modular system for XRF and XRD applications consisting of a microfocus X-ray source and different capillary optics," X-ray Spectrometry, vol. 33 (2004), pp. 312-316.
Bjeoumikhov et al., "Capillary Optics for X-Rays," Ch. 18 of "Modern Developments in X-Ray and Neutron Optics," A. Erko et al., eds. (Springer, Berlin, Germany, 2008), pp. 287-306.
Canberra Model S-5005 WinAxil X-Ray Analysis Software, published by: Canberra Eurisys Benelux N.V./S.A.,Zellik, Belgium; Jun. 2004.
Cerrina, "The Schwarzschild Objective," Ch. 27 of "Handbook of Optics vol. III, 2nd Ed." (McGraw Hill, New York, 2001).
Chen et al., "Advance in detection of low sulfur content by wavelength dispersive XRF," Proceedings of the Annual ISA Analysis Division Symposium (2002).
Chen et al., "Doubly curved crystal (DCC) X-ray optics and applications," Powder Diffraction, vol. 17(2) (2002), pp. 99-103.
Chen et al., "Guiding and focusing neutron beams using capillary optics," Nature vol. 357 (Jun. 4, 1992), pp. 391-393.
Chervenak et al., "Experimental thick-target bremsstrahlung spectra from electrons in the range 10 to 30 keV", Phys. Rev. A vol. 12 (1975), pp. 26-33.
Coan et al., "In vivo x-ray phase contrast analyzer-based imaging for longitudinal osteoarthritis studies in guinea pigs," Phys. Med. Biol. vol. 55(24) (2010), pp. 7649-7662.
Cockcroft et al., "Chapter 2: Experimental Setups," Powder Diffraction: Theory and Practice, R.E. Dinnebier and S.J.L. Billinge, eds (Royal Society of Chemistry Publishing, London, UK, 2008).
Cohen et al., "Tunable laboratory extended x-ray absorption fine structure system," Rev. Sci. Instr. vol. 51, No. 3, Mar. 1980, pp. 273-277.
Cong et al., "Fourier transform-based iterative method for differential phase-contrast computed tomography", Opt. Lett. vol. 37 (2012), pp. 1784-1786.
Cornaby et al., "Advances in X-ray Microfocusing with Monocapillary Optics at CHESS," CHESS News Magazine (2009), pp. 63-66.
Cornaby et al., "Design of Single-Bounce Monocapillary X-ray Optics," Advances in X-ray Analysis: Proceedings of the 55th Annual Conference on Applications of X-ray Analysis, vol. 50, (International Centre for Diffraction Data (ICDD), 2007), pp. 194-200.
Cornaby, "The Handbook of X-ray Single Bounce Monocapillary Optics, Including Optical Design and Synchrotron Applications" (PhD Dissertation, Cornell University, Ithaca, NY, May 2008).
David et al., "Fabrication of diffraction gratings for hard x-ray phase contrast imaging," Microelectron. Eng. vol. 84, (2007), pp. 1172-1177.
David et al., "Hard X-ray phase imaging and tomography using a grating interferometer," Spectrochimica Acta Part B vol. 62 (2007) pp. 626-630.
Davis et al., "Bridging the Micro-to-Macro Gap: A New Application for Micro X-Ray Fluorescence," Microsc Microanal., vol. 17(3) (Jun. 2011), pp. 410-417.
Diaz et al., "Monte Carlo Simulation of Scatter Field for Calculation of Contrast of Discs in Synthetic CDMAM Images," In: Digital Mammography, Proceedings 10th International Workshop IWDM 2010 (Springer Verlag, Berlin Heidelberg), (2010), pp. 628-635 (9 pages). Jun. 18, 2010.
Ding et al., "Reactive Ion Etching of CVD Diamond Films for MEMS Applications," Micromachining and Microfabrication, Proc. SPIE vol. 4230 (2000), pp. 224-230.
Dobrovinskaya et al., "Thermal Properties," Sect. 2.1.5 of "Sapphire: Material, Manufacturing,, Applications" (Springer Science + Business Media, New York, 2009).
Dong et al., "Improving Molecular Sensitivity in X-Ray Fluorescence Molecular Imaging (XFMI) of Iodine Distribution in Mouse-Sized Phantoms via Excitation Spectrum Optimization," IEEE Access, vol. 6, pp. 56966-56976 (2018).
Erko et al., "X-ray Optics," Ch. 3 of "Handbook of Practical X-Ray Fluorescence Analysis," B. Beckhoff et al., eds. (Springer, Berlin, Germany, 2006), pp. 85-198.
Falcone et al., "New directions in X-ray microscopy," Contemporary Physics, vol. 52, No. 4, (Jul.-Aug. 2010), pp. 293-318.

(56) References Cited

OTHER PUBLICATIONS

Fernández-Ruiz, "TXRF Spectrometry as a Powerful Tool for the Study of Metallic Traces in Biological Systems," Development in Analytical Chemistry, vol. 1 (2014), pp. 1-14.
Freund, "Mirrors for Synchrotron Beamlines," Ch. 26 of "Handbook of Optics vol. III, 2nd Ed." (McGraw Hill, New York, 2001).
Ge et al., "Investigation of the partially coherent effects in a 2D Talbot interferometer," Anal. Bioanal. Chem. vol. 401, (2011), pp. 865-870. Apr. 29, 2011 pub Jun. 14, 2011.
Gibson et al., "Polycapillary Optics: An Enabling Technology for New Applications," Advances in X-ray Analysis, vol. 45 (2002), pp. 286-297.
Gonzales et al., "Angular Distribution of Bremsstrahlung Produced by 10-Kev and 20 Kev Electrons Incident on a Thick Au Target", in Application of Accelerators in Research and Industry, AIP Conf. Proc. 1221 (2013), pp. 114-117.
Gonzales et al., "Angular distribution of thick-target bremsstrahlung produced by electrons with initial energies ranging from 10 to 20 keV incident on Ag", Phys. Rev. A vol. 84 (2011): 052726.
Guttmann et al., "Ellipsoidal capillary as condenser for the BESSSY full-field x-ray microscope," J. Phys. Conf. Ser. vol. 186 (2009): 012064.
Harasse et al., "Iterative reconstruction in x-ray computed laminography from differential phase measurements", Opt. Express. vol. 19 (2011), pp. 16560-16573.
Harasse et al., "X-ray Phase Laminography with a Grating Interferometer using Iterative Reconstruction", in International Workshop on X-ray and Neutron Phase Imaging with Gratings, AIP Conf. Proc. vol. 1466, (2012), pp. 163-168.
Harasse et al., "X-ray Phase Laminography with Talbot Interferometer", in Developments in X-Ray Tomography VII, Proc. SPIE vol. 7804 (2010), 780411.
Hasse et al., "New developments in laboratory-based x-ray sources and optics," Adv. in Laboratory-based X-Ray Sources, Optics, and Applications VI, ed. A.M. Khounsary, Proc. SPIE vol. 10387, 103870B-1 (2017).
Hemraj-Benny et al., "Near-Edge X-ray Absorption Fine Structure Spectroscopy as a Tool for Investigating Nanomaterials," Small, vol. 2(1), (2006), pp. 26-35.
Henke et al., "X-ray interactions: photoabsorption, scattering, transmission, and reflection at E=50-30000 eV, Z=1-92," Atomic Data and Nuclear Data Tables, vol. 54 (No. 2) (Jul. 1993), pp. 181-342.
Honma et al., Full-automatic XAFS Measurement System of the Engineering Science Research II beamline BL14B2 at Spring-8, 2011, AIP Conference Proceedings 1234, pp. 13-16.
Howard et al., "High-Definition X-ray Fluorescence Elemental Mapping of Paintings," Anal. Chem., 2012, vol. 84(7), pp. 3278-3286.
Howells, "Gratings and Monochromators in the VUV and Soft X-RAY Spectral Region," Ch. 21 of Handbook of Optics vol. III, 2nd Ed. (McGraw Hill, New York, 2001).
Howells, "Mirrors for Synchrotron-Radiation Beamlines," Publication LBL-34750 (Lawrence Berkeley Laboratory, Berkeley, CA, Sep. 1993).
Hrdý et al, "Diffractive-Refractive Optics: X-ray Crystal Monochromators with Profiled Diffracting Surfaces," Ch. 20 of "Modern Developments in X-Ray and Neutron Optics," A. Erko et al., eds. (Springer, Berlin Heidelberg New York, 2008).
Hwang et al, "New etching process for device fabrication using diamond," Diamond & Related Materials, vol. 13 (2004) pp. 2207-2210.
Ide-Ektessabi et al., "The role of trace metallic elements in neurodegenerative disorders: quantitative analysis using XRF and XANES spectroscopy," Anal. Sci., vol. 21(7) (Jul. 2005), pp. 885-892.
Ihsan et al., "A microfocus X-ray tube based on a microstructured X-ray target", Nuclear Instruments and Methods in Physics Research B vol. 267 (2009) pp. 3566-3573.
Ishisaka et al., "A New Method of Analyzing Edge Effect in Phase Contrast Imaging with Incoherent X-rays," Optical Review, vol. 7, No. 6, (2000), pp. 566-572.
Ito et al., "A Stable in-Laboratory EXAFS Measurement System," Jap. J. Appl. Phys., vol. 22, No. 2, Feb. 1, 1983, pp. 357-360.
Itoh et al., "Two-dimensional grating-based X-ray phase-contrast imaging using Fourier transform phase retrieval," Op. Express, vol. 19, No. 4 (2011) pp. 3339-3346.
Janssens et al, "Recent trends in quantitative aspects of microscopic X-ray fluorescence analysis," TrAC Trends in Analytical Chemistry 29.6 (Jun. 2010): 464-478.
Jiang et al., "X-Ray Phase-Contrast Imaging with Three 2D Gratings," Int. J. Biomed. Imaging, (2008), 827152, 8 pages.
Joy, "Astronomical X-ray Optics," Ch. 28 of "Handbook of Optics vol. III, 2nd Ed.," (McGraw Hill, New York, 2001).
Keyrilainen et al., "Phase contrast X-ray imaging of breast," Acta Radiologica, vol. 51 (8), (2010), pp. 866-884. Jan. 18, 2010 pub Jun. 15, 2010.
Kidalov et al., "Thermal Conductivity of Diamond Composites," Materials, vol. 2 (2009) pp. 2467-2495.
Kido et al., "Bone Cartilage Imaging with X-ray Interferometry using a Practical X-ray Tube", in Medical Imaging 2010: Physics of Medical Imaging, Proc. SPIE vol. 7622 (2010), 762240.
Kim, "Talbot images of wavelength-scale amplitude gratings," Opt. Express vol. 20(5), (2012), pp. 4904-4920.
Kirkpatrick et al., "Formation of Optical Images by X-Rays", J. Opt. Soc. Am. vol. 38(9) (1948), pp. 766-774.
Kirz, "Phase zone plates for x rays and the extreme uv," J. Op. Soc. Am. vol. 64 (Mar. 1974), pp. 301-309.
Kirz et al., "The History and Future of X-ray Microscopy", J. Physics: Conden. Series vol. 186 (2009): 012001.
Kiyohara et al., "Development of the Talbot-Lau Interferometry System Available for Clinical Use", in International Workshop on X-ray and Neutron Phase Imaging with Gratings, AIP Cong. Proc. vol. 1466, (2012), pp. 97-102.
Klockenkämper et al., "7.1 Instrumental Developments" and "7.3 Future Prospects by Combinations," from Chapter 7 of Total Reflection X-ray Fluorescence Analysis and Related Methods 2nd Ed. (J. Wiley and Sons, Hoboken, NJ, 2015).
Klockenkämper et al., "Chapter 3: Instrumentation for TXRF and GI-XRF," Total Reflection X-ray Fluorescence Analysis and Related Methods 2nd Ed. (J. Wiley and Sons, Hoboken, NJ, 2015).
Kottler et al., "A two-directional approach for grating based differential phase contrast imaging using hard x-rays," Opt. Express vol. 15(3), (2007), pp. 1175-1181.
Kottler et al., "Dual energy phase contrast x-ray imaging with Talbot-Lau interferometer," J. Appl. Phys. vol. 108(11), (2010), 114906. Jul. 7, 2010 pub Dec. 7, 2010.
Kumakhov et al., "Multiple reflection from surface X-ray optics," Physics Reports, vol. 191(5), (1990), pp. 289-350.
Kumakhov, "X-ray Capillary Optics. History of Development and Present Status" in Kumakhov Optics and Application, Proc. SPIE 4155 (2000), pp. 2-12.
Kuwabara et al., "Hard-X-ray Phase-Difference Microscopy with a Low-Brilliance Laboratory X-ray Source", Appl. Phys. Express vol. 4 (2011) 062502.
Kuznetsov, "X-Ray Optics Calculator," Institute of Microelectronics Technology and High Purity Materials, Russian Academy of Sciences (IMT RAS), Chernogolovka, Russia (6 pages submitted); 2016.
Lagomarsino et al., "Reflective Optical Arrays," Ch. 19 of "Modern Developments in X-Ray and Neutron Optics," A. Erko et al. eds. (Springer, Berlin, Germany, 2008), pp. 307-317.
Lai, "X-Ray Microfocusing Optics," Slide Presentation from Argonne National Laboratory, 71 slides, Cheiron Summer School 2007.
Langhoff et al., "X-ray Sources," Ch. 2 of "Handbook of Practical X-Ray Fluorescence Analysis," B. Beckhoff et al., eds. (Springer, Berlin Heidelberg New York, 2006), pp. 33-82.
Lechner et al., "Silicon drift detecors for high count rate X-ray spectroscopy at room temperature," Nuclear Instruments and Methods, vol. 458A (2001), pp. 281-287.
Leenaers et al., "Application of Glancing Incidence X-ray Analysis," 1997, X-ray Spectrometry, vol. 26, pp. 115-121.

(56) References Cited

OTHER PUBLICATIONS

Lengeler et al., "Refractive X-ray Optics," Ch. 20 of "Handbook of Optics vol. III, 2nd Ed." (McGraw Hill, New York, 2001.

Li et al., "Source-optic-crystal optimisation for compact monochromatic imaging," Proc. SPIE 5537 (2004), pp. 105-114.

Lohmann et al., "An interferometer based on the Talbot effect," Optics Communications vol. 2 (1971), pp. 413-415.

MacDonald et al., "An Introduction to X-ray and Neutron Optics," Ch. 19 of "Handbook of Optics vol. III, 2nd Ed." (McGraw Hill, New York, 2001).

MacDonald et al., "Polycapillary and Multichannel Plate X-Ray Optics," Ch. 30 of "Handbook of Optics vol. III, 2nd Ed.," (McGraw Hill, New York, 2001).

MacDonald et al., "Polycapillary X-ray Optics for Microdiffraction," J. Appl. Cryst., vol. 32 (1999) pp. 160-167.

MacDonald, "Focusing Polycapillary Optics and Their Applications," X-Ray Optics and Instrumentation, vol. 2010, (Oct. 2010): 867049.

Maj et al., "Etching methods for improving surface imperfections of diamonds used for x-ray monochromators," Adv. X-ray Anal., vol. 48 (2005), pp. 176-182.

Malgrange, "X-ray Optics for Synchrotron Radiation," ACTA Physica Polinica A, vol. 82(1) (1992) pp. 13-32.

Masuda et al., "Fabrication of Through-Hole Diamond Membranes by Plasma Etching Using Anodic Porous Alumina Mask," Electrochemical and Solid-State Letters, vol. 4(11) (2001) pp. G101-G103.

Matsushita, "Mirrors and Multilayers," Slide Presentation from Photon Factor, Tsukuba, Japan, 65 slides, (Cheiron School 2009, Sprint-8, Japan, Nov. 2009).

Matsushita, "X-ray monochromators," Slide Presentation from Photon Factory, Tsukuba, Japan, 70 slides, (Cheiron School 2009, Spring-8, Japan, Nov. 2009).

Matsuyama et al., "Wavefront measurement for a hard-X-ray nanobeam using single-grating interferometry", Opt Express vol. 20 (2012), pp. 24977-24986.

Miao et al., "Motionless phase stepping in X-ray phase contrast imaging with a compact source," Proceedings of the National Academy of Sciences, vol. 110(48), (2013), pp. 19268-19272.

Michette, "Zone and Phase Plates, Bragg-Fresnel Optics," Ch. 23 of "Handbook of Optics vol. III, 2nd Ed.," (McGraw Hill, New York, 2001).

Mizutani et al., X-ray microscopy for neural circuit reconstruction in 9th International Conference on X-Ray Microscopy, J. Phys: Conf. Ser. 186 (2009) 012092.

Modregger et al., "Grating-Based X-ray Phase Contrast Imaging," Ch. 3 of Emerging Imaging Technologies in Medicine, M. Anastasio & P. La Riviere, ed., CRC Press, Boca Raton, FL, (2012), pp. 43-56.

Momose et al., "Biomedical Imaging by Talbot-Type X-Ray Phase Tomography" in Developments in X-Ray Tomography V, Proc. SPIE vol. 6318 (2006) 63180T.

Momose et al., "Grating-Based X-ray Phase Imaging Using Multiline X-ray Source", Jpn. J. Appl. Phys. vol. 48 (2009), 076512.

Momose et al., "Phase Tomography by X-ray Talbot Interferometry for Biological Imaging" Jpn. J. Appl. Phys. vol. 45 2006 pp. 5254-5262.

Momose et al., "Phase Tomography Using X-ray Talbot Interferometer", in Synchrotron Radiation Instrumentation: Ninth International Conference, AIP Conf. Proc. vol. 879 (2007), pp. 1365-1368.

Momose et al., "Phase-Contrast X-Ray Imaging Using an X-Ray Interferometer for Biological Imaging", Analytical Sciences vol. 17 Supplement (2001), pp. i527-i530.

Momose et al., "Sensitivity of X-ray Phase Imaging Based on Talbot Interferometry", Jpn. J. Appl. Phys. vol. 47 (2008), pp. 8077-8080.

Momose et al., "X-ray Phase Measurements with Talbot Interferometry and Its Applications", in International Conference on Advanced Phase Measurement Methods in Optics and Imaging, AIP Conf. Proc. vol. 1236 (2010), pp. 195-199.

Momose et al., "X-ray Phase Imaging—From Static Observation to Dynamic Observation-", in International Workshop on X-ray and Neutron Phase Imaging with Gratings AIP Conf. Proc. vol. 1466, (2012), pp. 67-77.

Momose et al., "X-ray Phase Imaging Using Lau Effect", Appl. Phys. Express vol. 4 (2011) 066603.

Momose et al., "X-Ray Phase Imaging with Talbot Interferometry", in "Biomedical Mathematics: Promising Directions in Imaging, Therapy Planning, and Inverse Problems", Y. Censor, M. Jiang & G.Wang, eds. (Medical Physics Publishing, Madison, WI, USA, 2010), pp. 281-320.

Momose et al., "X-ray phase tomography with a Talbot interferometer in combination with an X-ray imaging microscope", in 9th International Conference on X-Ray Microscopy, J. Phys: Conf. Ser. 186 (2009) 012044.

Momose et al., "X-ray Talbot Interferometry with Capillary Plates", Jpn. J. Appl. Phys. vol. 45 (2006), pp. 314-316.

Momose et al., "Four-dimensional X-ray phase tomography with Talbot interferometry and white synchrotron radiation: dynamic observation of a living worm", Opt. Express vol. 19 (2011), pp. 8423-8432.

Momose et al., "High-speed X-ray phase imaging and X-ray phase tomography with Talbot interferometer and white synchrotron radiation", Opt. Express vol. 17 (2009), pp. 12540-12545.

Momose et al., "Phase Imaging with an X-ray Talbot Interferometer", Advances in X-ray Analysis vol. 49(3) (2006), pp. 21-30.

Momose et al.,"Demonstration of X-Ray Talbot Interferometry", Jpn. J. Appl. Phys. vol. 42 (2003), pp. L866-L868.

Momose et al.,"Phase Tomography Using an X-ray Talbot Interferometer", in Developments in X-Ray Tomography IV, Proc. SPIE vol. 5535 (2004), pp. 352-360.

Momose, "Recent Advances in X-ray Phase Imaging", Jpn. J. Appl. Phys. vol. 44 (2005), pp. 6355-6367.

Montgomery, "Self Imaging Objects of Infinite Aperture," J. Opt. Soc. Am. vol. 57(6), (1967), pp. 772-778.

Morimoto et al., "Development of multiline embedded X-ray targets for X-ray phase contrast imaging," XTOP 2012 Book of Abstracts, (Ioffe Physical-Technical Institute of the Russian Academy of Sciences, St. Petersburg, Russia, 2012), pp. 74-75.

Morimoto et al., X-ray phase contrast imaging by compact Talbot-Lau interferometer with a signal transmission grating, 2014, Optics Letters, vol. 39, No. 15, pp. 4297-4300.

Munro et al., Design of a novel phase contrast imaging system for mammography, 2010, Physics in Medicine and Biology, vol. 55, No. 14, pp. 4169-4185.

Nango et al., "Talbot-defocus multiscan tomography using the synchrotron X-ray microscope to study the lacuno-canalicular network in mouse bone", Biomed. Opt. Express vol. 4 (2013), pp. 917-923.

Neuhausler et al., "Non-destructive high-resolution X-ray imaging of ULSI micro-electronics using keV X-ray microscopy in Zernike phase contrast," Microelectronic Engineering, Elsevier Publishers BV., Amsterdam, NO, vol. 83, No. 4-9 (Apr. 1, 2006) pp. 1043-1046.

Newville, "Fundamentals of XAFS," (Univ. of Chicago, Chicago, IL, Jul. 23, 2004).

Noda et al., "Fabrication of Diffraction Grating with High Aspect Ratio Using X-ray Lithography Technique for X-ray Phase Imaging," Jpn. J. Appl. Phys. vol. 46, (2007), pp. 849-851.

Noda et al., "Fabrication of High Aspect Ratio X-ray Grating Using X-ray Lithography" J. Solid Mech_Mater. Eng. vol. 3 (2009), pp. 416-423.

Nojeh, "Carbon Nanotube Electron Sources: From Electron Beams to Energy Conversion and Optophononics", ISRN Nanomaterials vol. 2014 (2014): 879827.

Nuhn, "From storage rings to free electron lasers for hard x-rays", J.A37 Phys.: Condens. Matter vol. 16 (2004), pp. S3413-S34121.

Nykanen et al., "X-ray scattering in full-field digital mammography," Med. Phys. vol. 30(7), (2003), pp. 1864-1873.

Oji et al., Automatic XAFS measurement system developed at BL14B2 in SPring-8, Available online Nov. 15, 2011, Journal of Synchrotron Radiation, vol. 19, pp. 54-59.

(56) References Cited

OTHER PUBLICATIONS

Olbinado et al., "Demonstration of Stroboscopic X-ray Talbot Interferometry Using Polychromatic Synchrotron and Laboratory X-ray Sources", Appl. Phys. Express vol. 6 (2013), 096601.
Ortega et al., "Bio-metals imaging and speciation in cells using proton and synchrotron radiation X-ray microspectroscopy," J. Royal Society Interface vol. 6 suppl. 5 (Oct. 6, 2009), pp. 6S649-58.
Otendal et al., A 9 keV electron-impact liquid-gallium-jet x-ray source, Rev. Sci. Instrum. vol. 79 (2008): 016102.
Oxford Instruments Inc., Series 5000 Model XTF5011 X-ray Tube information, Jun. 1998, 3 pages.
Parrill et al., "GISAXS—Glancing Incidence Small Angle X-ray Scattering," Journal de Physique IV, vol. 3 (Dec. 1993), pp. 411-417.
PAXSCAN Flat Panel X-ray Imaging, Varian Sales Brochure, (Varian Medical Systems, Palo Alto, CA, Nov. 11, 2004).
Pfeiffer et al., "Hard-X-ray dark-field imaging using a grating interferometer," Nature Materials vol. 7, (2008), pp. 134-137.
Pfeiffer et al., "Hard x-ray phase tomography with low brilliance x-ray sources," Phys. Rev. Lett. vol. 98, (2007), 108105.
Pfeiffer et al., "Phase retrieval and differential phase-contrast imaging with low-brilliance X-ray sources," Nature Physics vol. 2, (2006), pp. 258-261.
Pfeiffer, "Milestones and basic principles of grating-based x-ray and neutron phase-contrast imaging," in International Workshop on X-ray and Neutron Phase Imaging with Gratings AIP Conf. Proc. vol. 1466, (2012), pp. 2-11.
Pianetta et al., "Application of synchrotron radiation to TXRF analysis of metal contamination on silicon wafer surfaces," Thin Solid Films, vol. 373(1-2), 2000, pp. 222-226.
Potts, "Electron Probe Microanalysis", Ch. 10 of "A Handbook of Silicate Rock Analysis" (Springer Science + Business Media, New York, 1987), pp. 326-382 (equation quoted from p. 336).
Prewitt et al., "FIB Repair of 5X Recticles and Effects on IC Quality," Integrated Circuit Metrology, Inspection, and Process Control VII, Proc. SPIE vol. 1926 (1993), pp. 517-526.
Prewitt et al., "Focused ion beam repair: staining of photomasks and reticles," J. Phys. D Appl. Phys. vol. 26 (1993), pp. 1135-1137.
Prewitt et al., "Gallium Staining in FIB Repair of Photomasks," Microelectronic Engineering, vol. 21 (1993), pp. 191-196.
Qin et al., "Trace metal imaging with high spatial resolution: Applications in biomedicine," Metallomics, vol. 3 (Jan. 2011), pp. 28-37.
Rayleigh, "On copying diffraction gratings and some phenomena connected therewith," Philos. Mag. vol. 11 (1881), pp. 196-205.
Renaud et al., "Probing surface and interface morphology with Grazing Incidence Small Angle X-ray Scattering," Surface Science Reports, vol. 64:8 (2009), pp. 255-380.
Riege, "Electron Emission from Ferroelectrics—A Review", CERN Report CERN AT/93-18 (CERN, Geneva, Switzerland, Jul. 1993).
Röntgen, Ueber eine neue Art von Strahlen (Wurzburg Verlag, Warzburg, Germany, 1896) also, in English, "On a New Kind of Rays," Nature vol. 53 (Jan. 23, 1896). pp. 274-276.
Rovezzi, "Study of the local order around magnetic impurities in semiconductors for spintronics." PhD Dissertation, Condensed Matter, Université Joseph-Fourier—Grenoble I, 2009, English <tel-00442852>.
Rutishauser, "X-ray grating interferometry for imaging and metrology," 2003, Eth Zurich, Diss. ETH No. 20939.
Sato et al., Two-dimensional gratings-based phase-contrast imaging using a conventional x-ray tube, 2011, Optics Letters, vol. 36, No. 18, pp. 3551-3553.
Scherer et al., "Bi-Directional X-Ray Phase-Contrast Mammography," PLoS One, vol. 9, Issue 5 (May 2014) e93502.
Scholz, "X-ray Tubes and Monochromators," Technical Workshop EPIV, Universität Würzburg (2007); 41 slides, 2007.
Scholze et al., "X-ray Detectors and XRF Detection Channels," Ch. 4 of "Handbook of Practical X-Ray Fluorescence Analysis," B. Beckhoff et al., eds. (Springer, Berlin Heidelberg, Germay, 2006), pp. 85-198.

Sebert, "Flat-panel detectors:how much better are they?" Pediatr. Radiol. vol. 36 (Suppl 2), (2006), pp. 173-181.
Shen, "Polarizing Crystal Optics," Ch. 25 of "Handbook of Optics vol. III, 2nd Ed.," (McGraw Hill, New York, 2001).
Shields et al., "Overview of Polycapillary X-ray Optics," Powder Diffraction, vol. 17(2) (Jun. 2002), pp. 70-80.
Shimura et al., "Hard x-ray phase contrast imaging using a tabletop Talbot-Lau interferometer with multiline embedded x-ray targets", Opt. Lett. vol. 38(2) (2013), pp. 157-159.
Siddons, "Crystal Monochromators and Bent Crystals," Ch. 22 of "Handbook of Optics vol. III, 2nd Ed.," (McGraw Hill, New York, 2001).
Smith, "Fundamentals of Digital Mammography:Physics, Technology and Practical Considerations," Publication R-BI-016 (Hologic, Inc., Bedford, MA, Mar. 2005).
Snigirev et al., "Hard X-Ray Microoptics," Ch. 17 of "Modern Developments in X-Ray and Neutron Optics," A. Erko et al., eds (Springer, Berlin, Germany, 2008), pp. 255-285.
Sparks Jr., "X-ray Fluorescence Microprobe for Chemical Analysis," in Synchrotron Radiation Research, H. Winick & S. Doniach, eds. (Plenum Press, New York, NY 1980), pp. 459-512.
Spiller, "Multilayers," Ch. 24 of "Handbook of Optics vol. III, 2nd Ed.," (McGraw Hill, New York, 2001).
Stampanoni et al., "The First Analysis and Clinical Evaluation of Native Breast Tissue Using Differential Phase-Contrast Mammography," Investigative Radiology, vol. 46, pp. 801-806. pub 2011-12-xx.
Strüder et al., "Silicon Drift Detectors for X-ray Imaging," Presentation at Detector Workshop on Synchrotron Radiation Instrumentation, 54 slides, (Argonne Nat'l Lab, Argonne, IL Dec. 8, 2005), available at: <http://www.aps.anl.gov/News/Conferences/2005/Synchrotron_Radiation_Instrumentation/Presentations/Strueder.pdf>.
Strüder et al., "X-Ray Detectors," Ch. 4 of "X-ray Spectrometry: Recent Technological Advances," K. Tsuji et al. eds. (John Wiley & Sons, Ltd. Chichester, West Sussex, UK, 2004), pp. 63-131.
Suzuki et al., "Hard X-ray Imaging Microscopy using X-ray Guide Tube as Beam Condenser for Field Illumination," J. Phys.: Conf. Ser. vol. 463 (2013): 012028.
Suzuki, "Development of the DIGITEX Safire Cardiac System Equipped with Direct conversion Flat Panel Detector," Digital Angio Technical Report (Shimadzu Corp., Kyoto, Japan, no date, published—2004 with product release).
Takahama, "RADspeed safire Digital General Radiography System Equipped with New Direct—Conversion FPD," Medical Now, No. 62 (2007),.
Takeda et al., "Differential Phase X-ray Imaging Microscopy with X-ray Talbot Interferometer" Appl. Phys. Express vol. 1 (2008) 117002.
Takeda et al., "X-Ray Phase Imaging with Single Phase Grating", Jpn. J. Appl. Phys. vol. 46 (2007), pp. L89-L91.
Takeda et al., "In vivo physiological saline-infused hepatic vessel imaging using a two-crystal-interferometer-based phase-contrast X-ray technique", J. Synchrotron Radiation vol. 19 (2012), pp. 252-256.
Talbot, "Facts relating to optical science no IV," Philos. Mag. vol. 9 (1836), pp. 401-407.
Tanaka et al., "Cadaveric and in vivo human joint imaging based on differential phase contrast by X-ray Talbot-Lau interferometry", Z. Med. Phys. vol. 23 (2013), pp. 222-227.
Tang et al., "Micro-computed tomography (Micro-CT): a novel appraoch for intraoperative breast cancer specimen imaging," Breast Cancer Res. Treat. vol. 139, pp. 311-316 (2013).
Taniguchi et al., "Diamond nanoimprint lithography," Nanotechnology, vol. 13 (2002) pp. 592-596.
Touzelbaev et al., "Applications of micron-scale passive diamond layers for the integrated circuits and microelectromechanical systems industries," Diamond and Rel. Mat'ls, vol. 7 (1998) pp. 1-14.
Tsuji et al., "X-Ray Spectrometry: Recent Technological Acvances," John Wiley & Sons Ltd. Chichester, West Susses, UK 2004), Chapters 1-7.
Udagawa, "An Introduction to in-House EXAFS Facilities," The Rigaku Journal, vol. 6, (1) (1989), pp. 20-27.

(56) References Cited

OTHER PUBLICATIONS

Udagawa, "An Introduction to X-ray Absorption Fine Structure," The Rigaku Journal, vol. 11(2)(1994), pp. 30-39.
Uehara et al., "Effectiveness of X-ray grating interferometry for non-destructive inspection of packaged devices", J. Appl. Phys. vol. 114 (2013), 134901.
Vogt, "X-ray Fluorescence Microscopy: A Tool for Biology, Life Science and Nanomedicine," Presentation on May 16, 2012 at James Madison Univ., Harrisonburg, VA (31 slides), 2012.
Wan et al.,"Fabrication of Multiple Slit Using Stacked-Sliced Method for Hard X-ray Talbot—Lau Interferometer", Jpn. J. Appl. Phys. vol. 47 (2008), pp. 7412-7414.
Wang et al., "Advantages of intermediate X-ray energies in Zernicke phase constrast X-ray microscopy," Biotech. Adv., vol. 31 (2013) pp. 387-392.
Wang et al., "Non-invasive classification of microcalcifications with phase-contrast X-ray mammography," Nature Comm. vol. 5:3797, pp. 1-9 (2014).
Wang, On the single-photon-counting (SPC) modes of imaging using an XFEL source, presented at IWORLD (2015).
Wang et al., "Precise patterning of diamond films for MEMS application" Journal of Materials Processing Technology vol. 127 (2002), pp. 230-233.
Weitkamp et al., "Design aspects of X-ray grating interferometry," in International Workshop on X-ray and Neutron Phase Imaging with Gratings AIP Conf. Proc. vol. 1466, (2012), pp. 84-89.
Weitkamp et al., "Hard X-ray phase imaging and tomography with a grating interferometer," Proc. SPIE vol. 5535, (2004), pp. 137-142.
Weitkamp et al., "X-ray wavefront diagnostics with Talbot interferometers," International Workshop on X-Ray Diagnostics and Scientific Application of the European XFEL, Ryn, Poland, (2010), 36 slides.
Weitkamp et al., Tomography with grating interferometers at low-brilliance sources, 2006, SPIE, vol. 6318, pp. 0S-1 to 0S-10.
Weitkamp et al., "X-ray phase imaging with a grating interferometer," Opt. Express vol. 13(16), (2005), pp. 6296-6304.
Weitkamp et al., "X-ray wavefront analysis and optics characterization with a grating interferometer," Appl. Phys. Lett. vol. 86, (2005), 054101.
Wen et al., "Fourier X-ray Scattering Radiography Yields Bone Structural Information," Radiology, vol. 251 (2009) pp. 910-918.
Wen et al., "Single-shot x-ray differential phase-contrast and diffraction imaging using two-dimensional transmission gratings," Op. Lett. vol. 35, No. 12, (2010) pp. 1932-1934.
Wobrauschek et al., "Energy Dispersive, X-Ray Fluorescence Analysis," Encyclopedia of Analytical Chemistry, R.A. Meyers, Ed. (Wiley 2010).
Wobrauschek et al., "Micro XRF of light elements using a polycapillary lens and an ultra-thin window Silicon Drift Detector inside a vacuum chamber," 2005, International Centre for Diffraction Data 2005, Advances in X-ray Analysis, vol. 48, pp. 229-235.
Wolter, "Spiegelsysteme streifenden Einfalls als abbildende Optiken fur Rontgenstrahlen" [Grazing Incidence Reflector Systems as Imaging Optics for X-rays] Annalen der Physik vol. 445, Issue 1-2 (1952), pp. 94-114.
X-ray-Optics.de Website, http://www.x-ray-optics.de/, accessed Feb. 13, 2016.
Yakimchuk et al., "Ellipsoidal Concentrators for Laboratory X-ray Sources: Analytical approaches for optimization," Mar. 22, 2013, Crystallography Reports, vol. 58, No. 2, pp. 355-364.
Yamamoto, "Fundamental physics of vacuum electron sources", Reports on Progress in Physics vol. 69, (2006), pp. 181-232.
Yanagihara et al., "X-Ray Optics," Ch. 3 of "X-ray Spectrometry: Recent Technological Advances," K. Tsuji et al. eds. (John Wiley & Sons, Ltd. Chichester, West Sussex, UK, 2004), pp. 63-131.
Yang et al., "Analysis of Intrinsic Stress in Diamond Films by X-ray Diffraction," Advances in X-ray Analysis, vol. 43 (2000), pp. 151-156.
Yashiro et al., "Distribution of unresolvable anisotropic microstructures revealed in visibility-contrast images using x-ray Talbot interferometry", Phys. Rev. B vol. 84 (2011), 094106.
Yashiro et al., "Hard x-ray phase-imaging microscopy using the self-imaging phenomenon of a transmission grating", Phys. Rev. A vol. 82 (2010), 043822.
Yashiro et al., "Theoretical Aspect of X-ray Phase Microscopy with Transmission Gratings" in International Workshop on X-ray and Neutron Phase Imaging with Gratings, AIP Conf. Proc. vol. 1466, (2012), pp. 144-149.
Yashiro et al., "X-ray Phase Imaging and Tomography Using a Fresnel Zone Plate and a Transmission Grating", in "The 10th International Conference on X-ray Microscopy Radiation Instrumentation", AIP Conf. Proc. vol. 1365 (2011) pp. 317-320.
Yashiro et al., "Efficiency of capturing a phase image using cone-beam x-ray Talbot interferometry", J. Opt. Soc. Am. A vol. 25 (2008), pp. 2025-2039.
Yashiro et al., "On the origin of visibility contrast in x-ray Talbot interferometry", Opt. Express (2010), pp. 16890-16901.
Yashiro et al., "Optimal Design of Transmission Grating for X-ray Talbot Interferometer", Advances in X-ray Analysis vol. 49(3) (2006), pp. 375-379.
Yashiro et al., "X-ray Phase Imaging Microscopy using a Fresnel Zone Plate and a Transmission Grating", in The 10th International Conference on Synchrotron Radiation Instrumentation, AIP Conf. Proc. vol. 1234 (2010), pp. 473-476.
Yashiro. et. al., "Hard-X-Ray Phase-Difference Microscopy Using a Fresnel Zone Plate and a Transmission Grating", Phys. Rev. Lett. vol. 103 (2009), 180801.
Yu et al., "Morphology and Microstructure of Tungsten Films by Magnetron Sputtering," Mat. Sci. Forum, vol. 913, pp. 416-423 (2018).
Zanette et al., "Two-Dimensional X-Ray Grating interferometer," Phys. Rev. Lett. vol. 105 (2010) pp. 248102-1 248102-4.
Zeng et al., "Ellipsoidal and parabolic glass capillaries as condensers for x-ray microscopes," Appl. Opt. vol. 47 (May 2008), pp. 2376-2381.
Zeng et al., "Glass Monocapillary X-ray Optics and Their Applications in X-Ray Microscopy," X-ray Optics and Microanalysis: Proceedings of the 20th International Congress, AIP Conf. Proc. vol. 1221, (2010), pp. 41-47.
Zhang et al., "Fabrication of Diamond Microstructures by Using Dry and Wet Etching Methods", Plasma Science and Technology vol. 15(6) (Jun. 2013), pp. 552-554.
Hennekam et al., "Trace metal analysis of sediment cores using a novel X-ray fluorescence core scanning method," Quaternary Int'l, https://doi.org/10.1016/j.quaint.2018.10.018 (2018).
Malzer et al., "A laboratory spectrometer for high throughput X-ray emission spectroscopy in catalysis research," Rev. Sci. Inst. 89, 113111 (2018).
Tkachuk et al., "High-resolution x-ray tomography using laboratory sources", in Developments in X-Ray Tomography V, Proc. SPIE 6318 (2006): 631810.
Tkachuk et al., "Multi-length scale x-ray tomography using laboratory and synchrotron sources", Microsc. Microanal. vol. 13 (Suppl. 2) (2007), pp. 1570-1571.
Viermetz et al., "High resolution laboratory grating-based X-ray phase-contrast CT," Scientific Reports 8:15884 (2018).

* cited by examiner

TALBOT X-RAY MICROSCOPE

CROSS-REFERENCE TO RELATED APPLICATIONS

This Patent Application claims the priority benefit of U.S. provisional patent application No. 62/485,916, titled "TALBOT X-RAY MICROSCOPE," filed Apr. 15, 2017, and is a continuation-in-part of U.S. patent application Ser. No. 14/712,917, filed May 15, 2015 and entitled "X-RAY METHOD FOR MEASUREMENT, CHARACTERIZATION, AND ANALYSIS OF PERIODIC STRUCTURES", which in turn is a continuation-in-part of U.S. patent application Ser. No. 14/700,137, filed Apr. 29, 2015 and entitled "X-RAY INTERFEROMETRIC IMAGING SYSTEM", which in turn is a continuation-in-part of U.S. patent application Ser. No. 14/527,523, filed Oct. 29, 2014 and entitled "X-RAY INTERFEROMETRIC IMAGING SYSTEM", which in turn claims the benefit of U.S. Provisional Patent Application Nos. 61/898,019, filed Oct. 31, 2013 and entitled "X-ray Phase Contrast imaging System"; 61/901,361, filed on Nov. 7, 2013 and entitled "An X-ray Source Consisting of an Array of Fine Sub-Sources"; and 61/981,098, filed Apr. 17, 2014 and entitled "Two Dimensional Phase Contrast Imaging Apparatus", the disclosures of all of which are incorporated herein by reference in their entirety. Application Ser. No. 14/712,917 also claims the benefit of 61/993,792 filed May 15, 2014 and entitled "Method of Talbot-Effect Based X-ray Patterned Probe and Characterization (Metrology or Inspection) Apparatuses Using Such", the disclosure of which is hereby incorporated by reference in its entirety.

BACKGROUND a. Field of the Invention

The present technology relates to interferometric systems using x-rays, and in particular, interferometric measurement, characterization and analysis systems using a system of periodic micro-beams to illuminate an object to determine various structural and chemical properties of the object.

b. Discussion of Prior Art

Prior art x-ray microscopes are generally limited by the resolution of the x-ray optics (e.g. zone plates) and/or the resolution of the pixel size of the detector. Although some commercial x-ray microscope systems have a resolution of less than 100 nm, such systems have an extremely limited field of view, and high resolution x-ray microscopy with a large field of view has difficulty producing images with a resolution smaller than 1 micron.

Talbot systems of the prior art have traditionally been used for low resolution imaging. What is needed is a microscopy system that utilizes Talbot interference fringes for high resolution imaging at improved throughput.

SUMMARY

This present technology, roughly described, includes systems for x-ray microscopy using an array of micro-beams having a micro- or nano-scale beam intensity profile to provide selective illumination of micro- or nano-scale regions of an object. An array detector is positioned such that each pixel of the detector only detects x-rays corresponding to a single micro-beam, allowing the signal arising from the x-ray detector to be identified with the specific, limited micro- or nano-scale regions illuminated. This enables microscopy while using a higher efficiency, larger pixel detector without compromising spatial resolution.

In embodiments, the micro- or nano-scale beams may be provided by producing a set of Talbot interference fringes, which creates a set of fine x-ray micro-beams corresponding to beam comprising the anti-nodes of the interference pattern. In some embodiments, the array of micro- or nano-beams may be provided by a conventional x-ray source and an array of x-ray imaging elements (e.g. x-ray lenses).

In embodiments, both the detector and the object are placed within the same waist or "depth-of-focus" range of a set of Talbot constructive fringes (anti-nodes). In some embodiments, the detector is placed downstream at any subsequent set of anti-nodes (an integer number of Talbot distances away). In some embodiments, the object is positioned on a mount that allows translation in the x- and y-directions perpendicular to the direction of x-ray beam propagation, allowing a "scanned" transmission image on a microscopic scale to be assembled. In some embodiments, the object is positioned on a mount that allows rotation about an axis perpendicular to the direction of x-ray beam propagation, allowing the collection of data on a microscopic scale to be used for laminographic or tomographic images reconstruction.

Additional masking layers may be inserted in the beam path to block a selected number of the micro-beams, allowing the use of detectors with larger pixel sizes for the remaining micro-beams. The use of a masking layer also allows the use of a detector with enhanced detection efficiency for the remaining micro-beams. Such masking layers may be placed in front of the object to be examined, between the object and the detector, or be designed as part of the detector structure itself.

DETAILED DESCRIPTION OF EMBODIMENTS OF THE INVENTION

This present technology includes systems for x-ray microscopy using an array of micro-beams having a micro- or nano-scale beam intensity profile to provide selective illumination of micro- or nano-scale regions of an object. Each micro-beam is separated from other micro-beams by regions of lower x-ray intensity, ranging from 0.8× to 0× of the intensity of the micro-beam. An array detector is positioned such that each pixel of the detector only detects x-rays corresponding to a single micro-beam, allowing the signal arising from the x-ray detector to be identified with the specific, limited micro- or nano-scale regions illuminated. In some instances, the object being imaged and the detector are positioned within the same Talbot diffraction order. In the present system, the spatial resolution is decoupled from the source size and the detector pixel size.

Imaging using Talbot fringes typically involves a grating (often a phase-shifting grating) to produce the Talbot interference pattern, and then analysis of the resulting pattern with a second grating and/or an array x-ray detector.

Figure 1A:
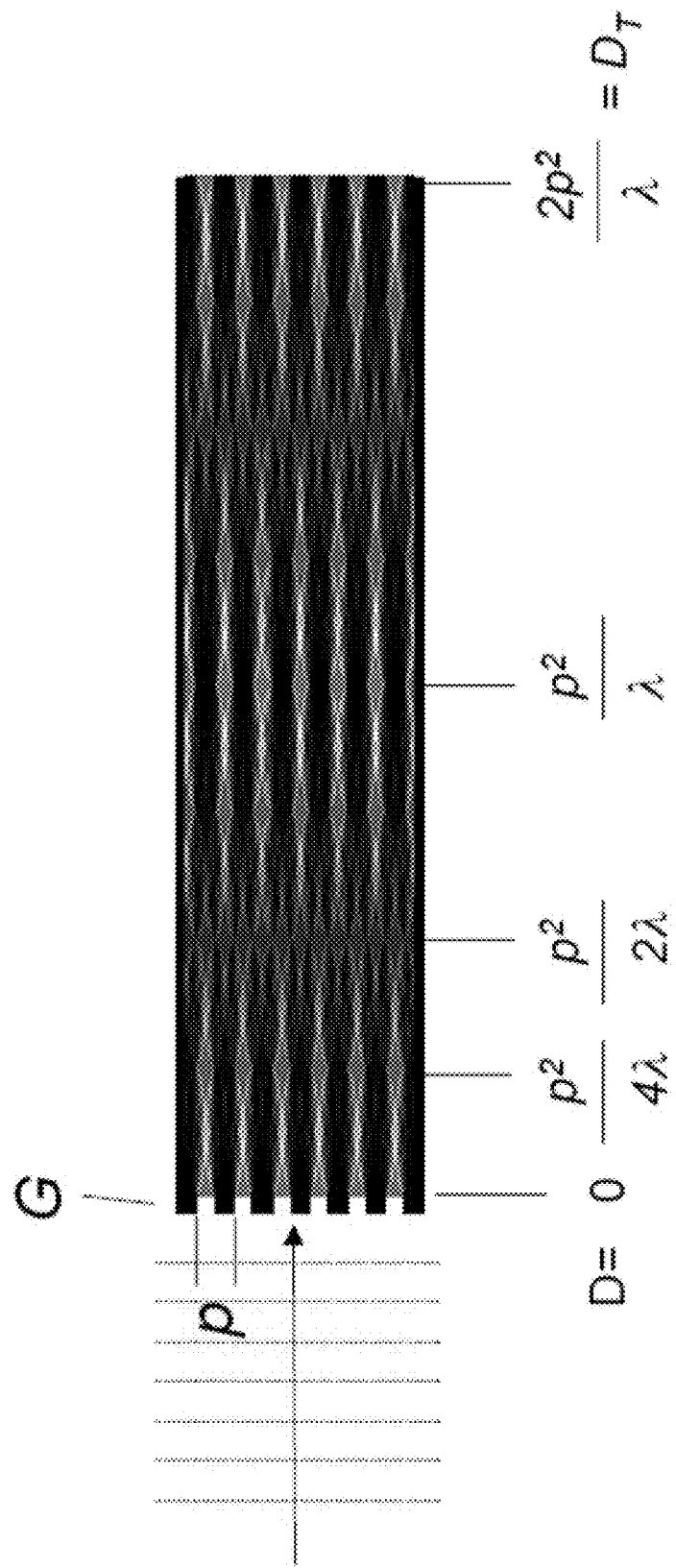
FIG. 1A illustrates a prior art example of a Talbot interference fringe pattern for a 1:1 duty cycle absorption grating.

FIG. 1A illustrates a Talbot interference fringe generated by an absorption grating G having a 50/50 duty cycle with a pitch p when illuminated by a plane wave. Interference fringes are generated behind the grating, reconstructing the pitch p with a 50/50 duty cycle at the Talbot distance $D_T$, given by $$D_T = \frac{2p_1^2}{\lambda} \quad \text{[Eqn. 1]}$$

where $p_1$ is the period of the beam splitting grating and $\lambda$ is the x-ray wavelength.

As an x-ray illuminator, the Talbot interference pattern can, with suitable selection of a beam-splitting grating, produce bright anti-nodes with corresponding micron-scale dimensions. For x-rays with an energy of 24.8 keV and an absorption grating with a 50/50 duty cycle and a 1 micron pitch, the Talbot distance is $D_T$=4 cm. The scales for the x- and y-directions of the fringes in the illustration of FIG. 1 are quite different, and although the fringes may laterally (i.e. perpendicular to the direction of propagation) have a micron scale and pitch, they can have depth-of-focus on the scale of hundreds of microns to even centimeters.

Fringe patterns at various fractional Talbot distances may actually be smaller than the size of the original grating features. These anti-nodes may therefore serve as the multiple micro-beams used for illuminating an object to achieve higher resolution.

The range (depth-of-focus) over which the anti-node maintains its finest dimension is related to the pitch p of the Talbot fringes by:

$$DOF \propto \frac{p^2}{2\lambda} \quad \text{[Eqn. 2]}$$

The waist, or "depth-of-focus" equivalent for the anti-node for x-rays of, for example, 20 keV and a grating period of 1 micron is on the order of centimeters.

Figure 1B:
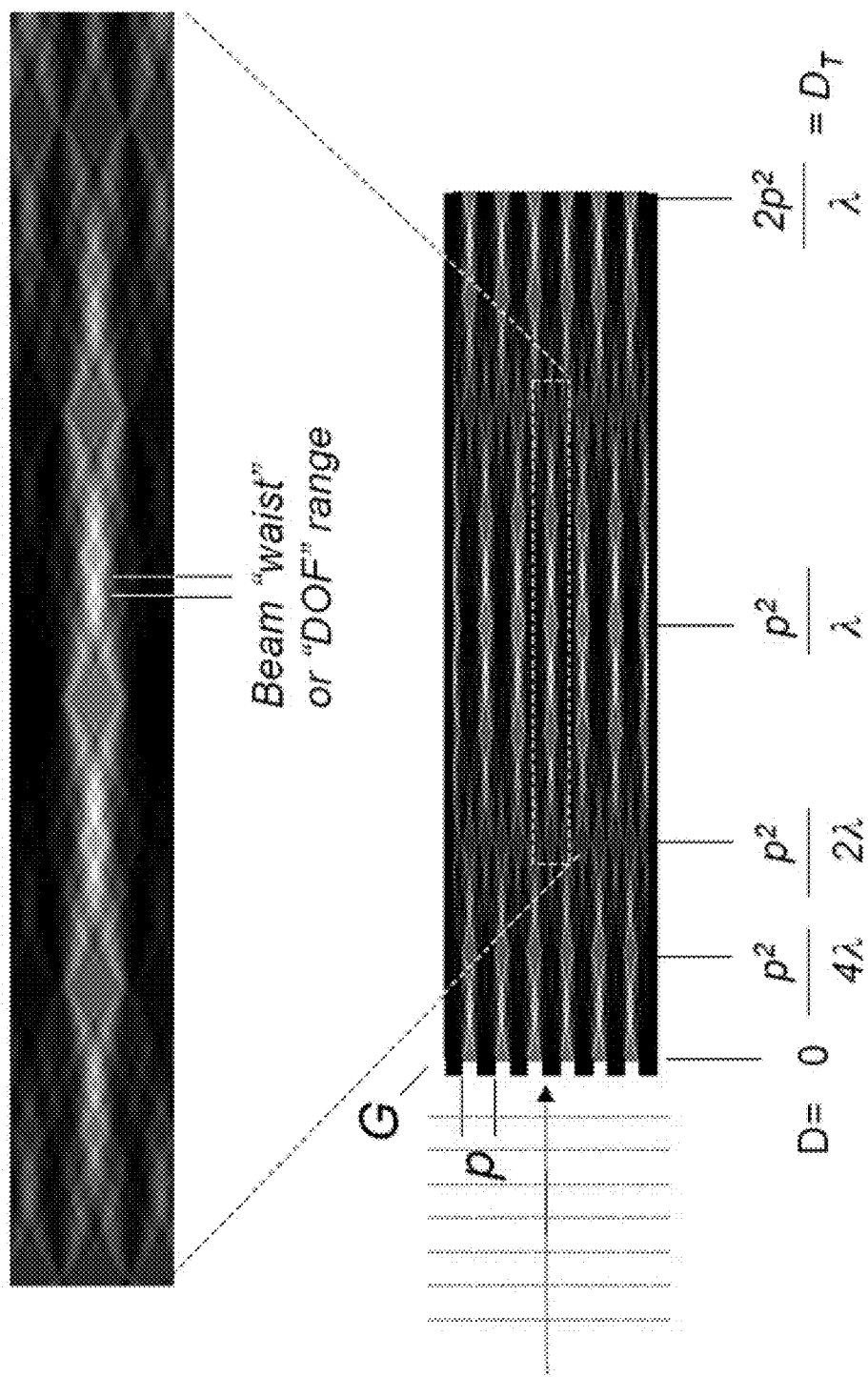
FIG. 1B illustrates a detail from the pattern of FIG. 1A showing an anti-node as a "depth-of-focus" range.

FIG. 1B illustrates an enlarged portion of an anti-node of FIG. 1A, with a portion that may be considered a DOFs of one of the anti-nodes noted. In some instances, an anti-node is a portion of the beam that differs from a node by greater than 20%; for example, the contrast ratio between an "anti-node" and "node" can be 1.2:1. Exact definitions of a beam "waist", defined by the range over which an anti-node varies by less than a predetermined amount (e.g. a length range over which the anti-node full-width at half-maximum variation is within 5%) may be defined for various Talbot patterns. Note that a given interference pattern may have many fine "waists" that can be used for illumination, and, depending on the grating used, some may be of even finer dimensions than the grating half-pitch. These "waists" may also occur at any number of distances from the grating and need not be at the previously defined fractional Talbot distances.

The pattern of Talbot fringes therefore resembles an array of "micro-beams" propagating in space. The fringes may be parallel micro-beams, as was illustrated in FIG. 1, or may be obtained using converging or diverging x-ray beams. Additional examples of Talbot interference patterns are shown in FIGS. 2A-2C.

Figure 2A:
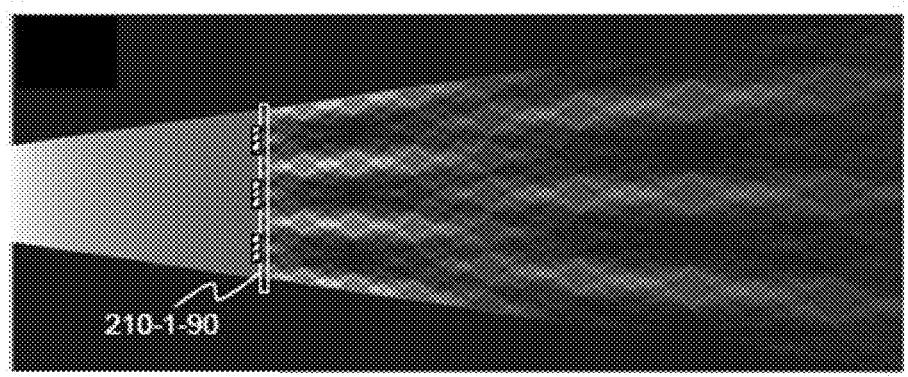
FIG. 2A illustrates a prior art example of a diverging Talbot interference fringe pattern for a 1:1 duty cycle $\pi/2$ phase shifting grating.
Figure 2B:
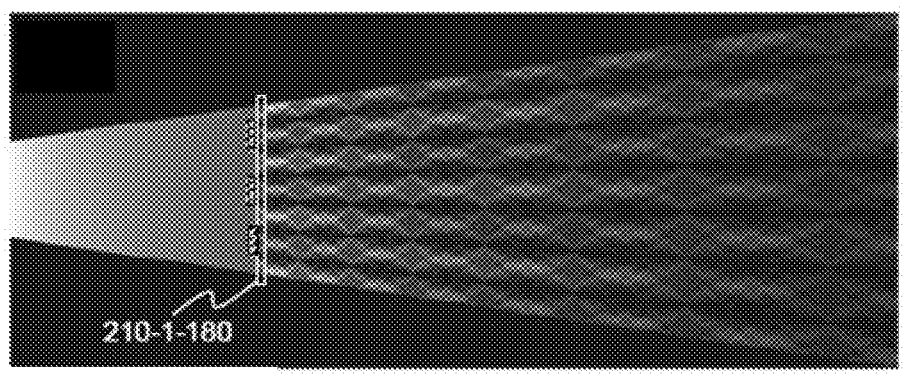
FIG. 2B illustrates a prior art example of a diverging Talbot interference fringe pattern for a 1:1 duty cycle $\pi$ phase shifting grating.
Figure 2C:
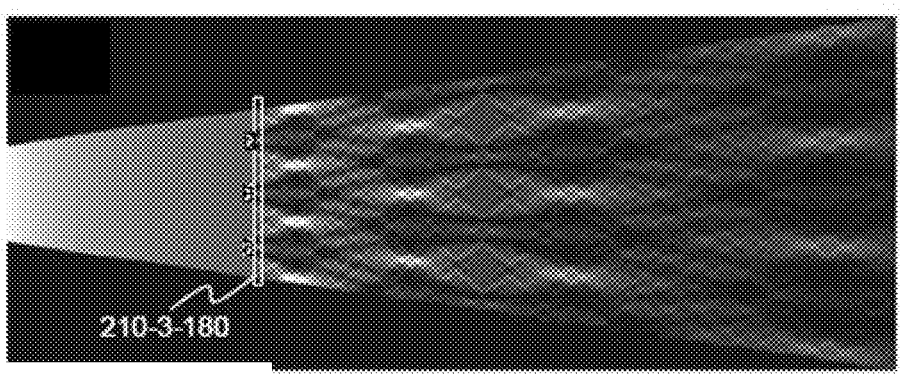
FIG. 2C illustrates a prior art example of a diverging Talbot interference fringe pattern for a 1:3 duty cycle $\pi$ phase shifting grating.

FIG. 2A illustrates the intensity pattern produced by a grating 210-1-90 (shown in cross section) introducing a π/2 radian phase shift from a 1:1 grating-to-space width ratio. FIG. 2B illustrates the intensity pattern produced by a grating 210-1-180 introducing a π radian phase shift in a 1:1 grating-to-space width ratio. FIG. 2C illustrates the intensity pattern produced by a grating 210-3-180 introducing a π radian phase shift in a 1:3 grating-to-space width ratio. Simulations of FIGS. 2A-2C assume gratings with a Ronchi (e.g. line/space square wave) profile and a point radiation source with sufficient spatial coherence.

Figure 2D:
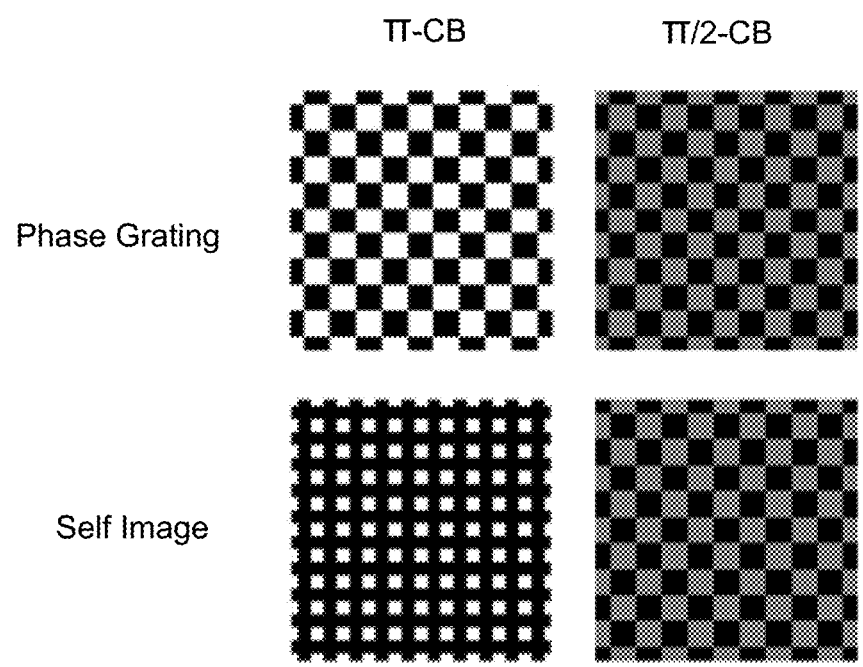
FIG. 2D illustrates phase gratings and self images for different phase grating periods.

FIG. 2D illustrates two-dimensional phase gratings and self images for phase grating periods of π and π/2. As shown in FIG. 2D, the π period grating is in the form of a checkerboard and produces a "mesh" self image. A grating with $\pi/2$ period also has checkerboard form but produces a checkerboard self-image with inverted contrast. The x-ray microscope of the present technology can utilize a grating with a period of $\pi$, $\pi/2$, or other period to produce micro-beams.

In many embodiments, this beam splitting diffraction grating is that of a phase grating of low absorption but producing considerable x-ray phase shift of either $\pi/2$ or $\pi$ radians, or some other specified or predetermined value such as a fraction of or multiple of $\pi$ or $\pi/2$. These gratings may be one-dimensional or two-dimensional. In some embodiments, the object being examined is placed downstream of the diffractive grating at a fractional Talbot distance $D_N$ represented by the equation $$D_N = N_a \frac{p_1^2}{8\lambda} = \frac{N_a}{16} D_T \qquad [\text{Eqn. 3}]$$

where $p_1$ is the period of the beam splitting grating, $D_N$ is the fractional Talbot distance for a plane wave illumination, $\lambda$ is the mean x-ray wavelength, and $N_a$ is the Talbot fractional order (N=1, 2, 3, . . . ) at which the object is placed. In some instances, the object is placed downstream of the diffractive grating at a distance that is not a fractional Talbot distance, but instead located at a distance wherein the wavefront is comprised of regions of anti-nodes and nodes that correspond to the periodic regions of interest for analysis.

Depending on the grating parameters (e.g. a $\pi$ phase shifting grating versus a $\pi/2$ phase shifting grating), optimal Talbot distances ($N_a$) may be chosen for interference patterns of interest or best suited for the application.

1. Talbot Fringes as an Array of Micro-Beams.

The microscope system and method of using it disclosed herein may be formed using any number of techniques that create an array of micro- or nano-scale x-ray beams used for illuminating an object. As an example, using an optical system to image either multiple arrayed x-ray sources or alternatively, an x-ray source having a transmission target with an array of microstructures, may provide "micro-beams" that correspond to the images of the source points within the depth of focus of the x-ray optical system.

Talbot fringes, especially those formed by a phase grating, are a highly efficient method of directing x-rays into a effective array of micro-beams. The effective lateral dimension of the Talbot anti-nodes (the beam diameter if the beams are constructed to be circular) can, using the appropriate beam-splitting grating to establish the fringes, be made to be very small (e.g. submicron, such as 20 nm or 300 nm). The Talbot interference pattern, when used to illuminate an object under investigation in transmission, provides an array of discrete micro- or nano-probes that can be detected and analyzed using an array detector. In this way, the x-ray microscope system can achieve submicron (e.g. 0.3 um) spatial resolution at high throughput. When the detector is selected to have a pixel size that corresponds to the pitch of the Talbot fringes, and both the object and the detector are placed within the effective "depth-of-focus" of the Talbot fringes, each pixel is detecting transmitted x-rays from a single one of the "micro-beams."

The contrast between the intensity of the plurality micro-beams and the regions between the micro-beams may be further improved by placing an absorbing grating of the same pitch as the micro-beams such that the x-rays between the micro-beams are attenuated.

As in the previously mentioned co-pending US Patent Applications and US Provisional Patent Applications, scanning the object in x- and y-dimensions allows the micro- or nano-scale probe to be moved over the object, and if the range of motion is as large as, or larger than, the Talbot fringe pitch, a high resolution "map" of the transmission of the object may be obtained with a relatively lower resolution x-ray pixel array detector. The "resolution" of the system is dictated solely by the size of the micro-beam, and is independent of the detector pixel size.

Figure 3A:
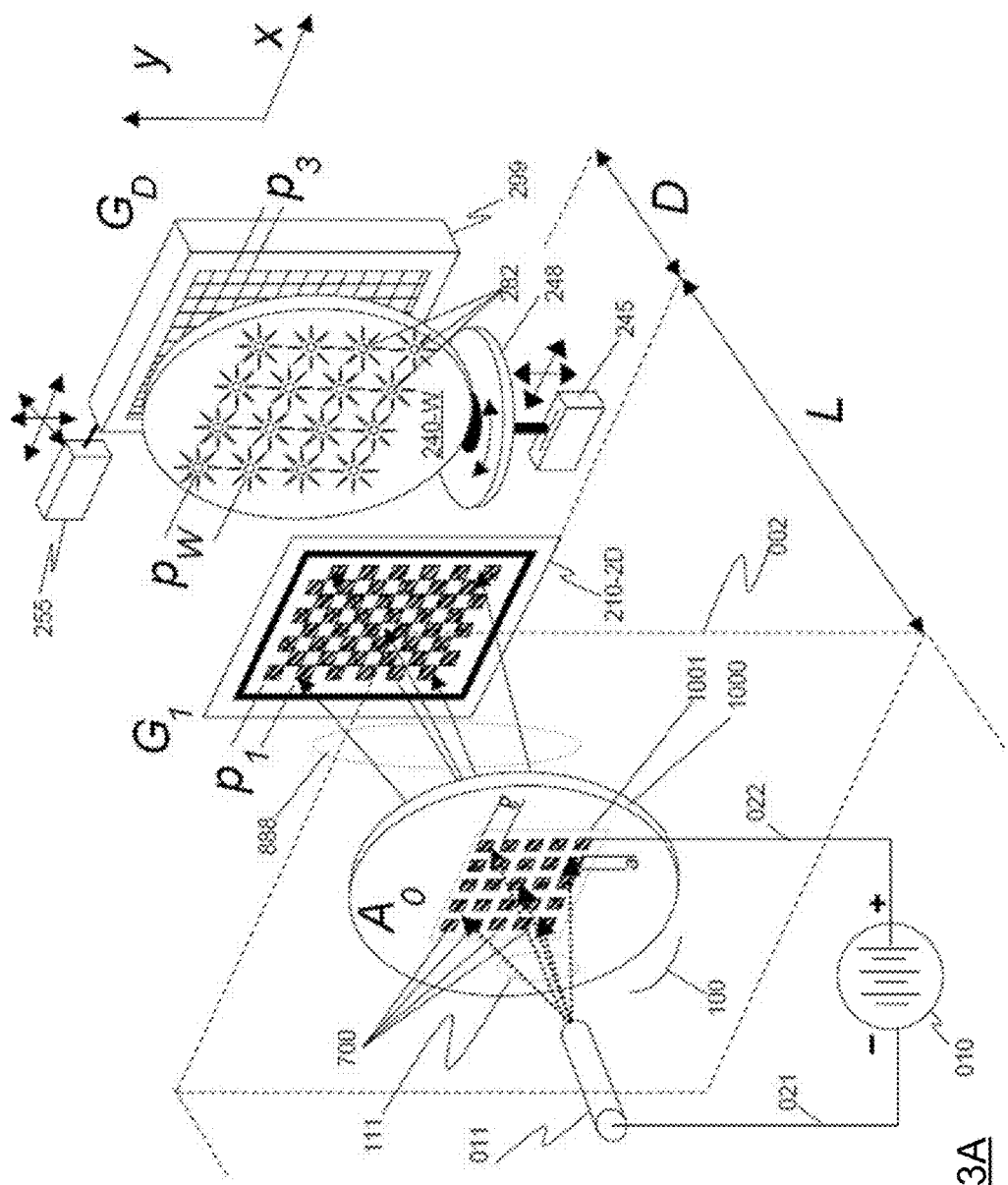
FIG. 3A illustrates a schematic view of a microscope according to an embodiment of the invention.
Figure 4A:
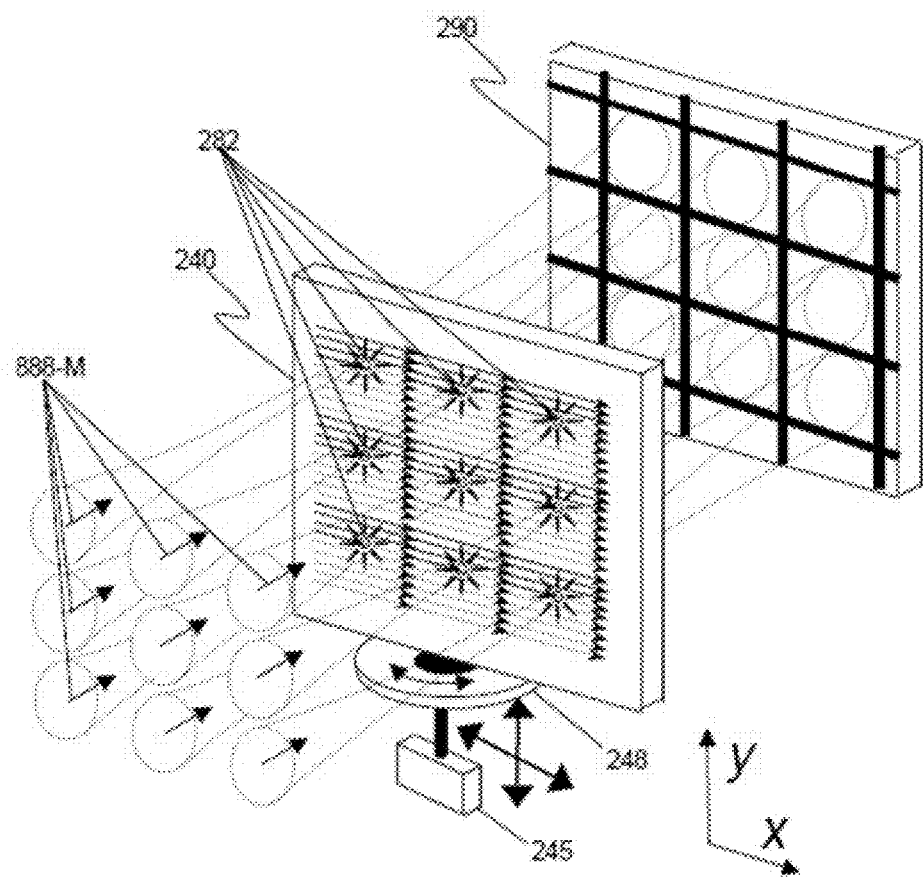
FIG. 4A illustrates a schematic view of the micro-beams, object, and detector of the embodiment of FIG. 3A.
Figure 4B:
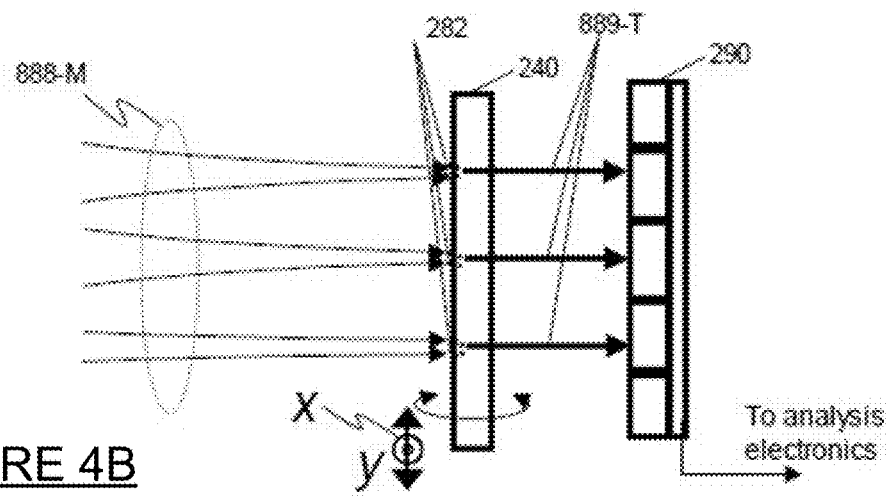
FIG. 4B illustrates a schematic cross-section view of the micro-beams, object, and detector of the embodiment of FIG. 3A.

A schematic for such a system is illustrated in FIG. 3A, and in more detail in FIGS. 4A and 4B. Source 011 provides electrons 111 to target 100 to generate an x-ray beam 888 which creates an array of microbeams after passing through a grating G1. The source of X-rays satisfies known constraints to realize the arrays of beamlets, preferably down to sub-micron size. The source of X-rays can be a single point or line source, or a periodic structured source such as a conventional source paired with an absorption (one- or two-dimensional) grating. Alternatively, a key development that yields increased throughput is decoupling the source size from the spatial resolution, which allows a large and consequently high power source to be used. One innovation of the present technology that enables greater x-ray power employs an x-ray source patterned according to a periodic pattern $A_0$. Such a system is illustrated in FIG. 3A. In this configuration as illustrated, an x-ray source 11 has a target 100 having a substrate 1000 and a region 1001 containing discrete microstructures 700 of element size a arranged in a periodic 2-D pattern with period $p_0$. When bombarded with electrons 111, these produce x-rays 888 in a periodic pattern with period $p_0$. In some instances, The target 100, which may include x-ray generating microstructures, x-ray blocking masks, and/or other elements described herein, can implement an x-ray generator.

Each microstructure 700 in target 100 of the structured source acts as an independent and mutually incoherent sub-source (or source points) of x-rays. The interference of these source points create a set of fringes in the sample plane that are laterally displaced with respect to the other source points. The pitch of the structured source and source to G1 distance can be selected to ensure that the fringes overlap in the sample plane. The increase in focused flux is proportional to the number of source points used.

In some instances, the source is sufficiently far from the G1 grating 210-2D to have a coherence length larger than the G1 grating period. If an individual sub-source apparent width is S, the distance between the source and G1 is Z and the radiation wavelength is L, then it holds that L*Z/S>p1 where p1 is the G1 period.

When an array of x-ray illumination beams (micro beams) 888-M is formed, the object 240 to be examined is illuminated at an array of discrete interaction locations 282. In many embodiments, the sample 248 is placed at a Talbot distance downstream of the beam-splitting grating. The positions can be scanned in x- and y-dimensions perpendicular to the direction of propagation of the micro-beams using a position controller 245, and the x-ray illumination beams 889-T resulting from the interaction of the micro-beams and the object can be detected by an array detector 290.

The array detector 290 will be aligned such that each pixel of the detector will be positioned to collect only x-rays corresponding to a single micro-beam. This is typically within the "depth of focus" of the anti-node. By pairing the use of multiple micro-beams paired with a detector having a pixel pitch matched to the pitch of the micro-beams, and aligned so that each pixel detects x-rays from only the interaction of a single micro-beam at a given position on the object, the equivalent of $10^2$ to $10^4$ parallel micro-beam detection systems can be created.

The object can then be scanned in x- and y-coordinates. This produces "maps" in parallel of the properties of the object, but the range of motion can be reduced to only correspond to the pitch of the micro-probes (although some overlap between scanned areas may be appropriate to provide a relative calibration between data collected for neighboring "maps"). The data in each point in the map is limited in resolution only by the lateral dimensions of the Talbot fringe, so a less expensive and/or more efficient detector with larger pixels can be used to collect high resolution images.

The "maps" generated by each pixel may then be stitched together digitally to produce a large-scale "macro-map" of the object properties, while reducing the corresponding data collection time by a factor related to the number of micro-beams (e.g. up to a factor of $10^4$).

To achieve some degree of tomographic analysis, limited angle adjustment of the object may also be added to the motion protocol, as long as the interaction of x-rays with the object as well as the corresponding detector pixel both remain within the depth-of-focus for all of the multiple micro-beams.

1.1 Alternative X-Ray Sources

Figure 3B:
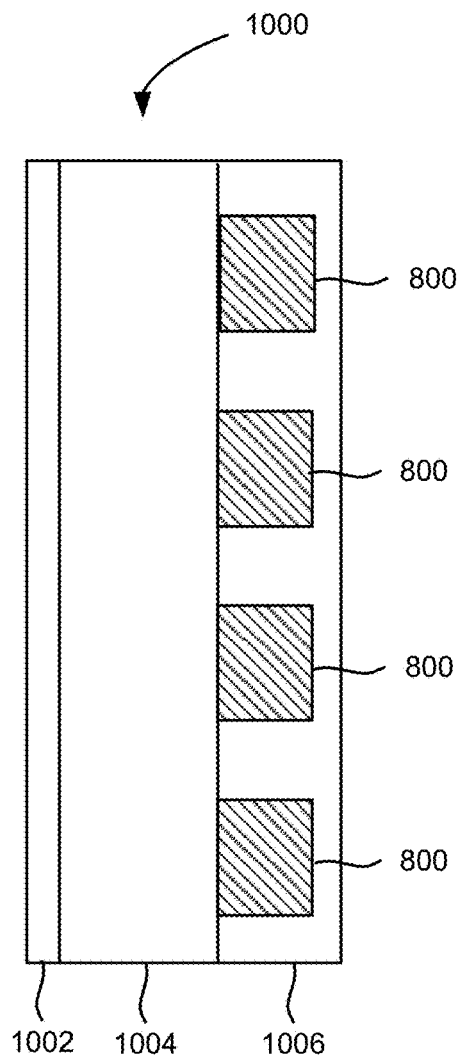
FIG. 3B illustrates a substrate with an embedded target mask.

In some instances, the x-ray source target may comprise a microstructured mask. FIG. 3B illustrates a substrate 1000 with an embedded microstructure mask. The substrate 1000 of FIG. 3B includes a thin film 1002, a first substrate portion 1004, and a second substrate portion 1006. The substrate portions 1004 and 1005 may be formed of low atomic element materials such as diamond, Be, sapphire, etc. An electron beam bombarding the thin film 1002 generates x-rays within the thin film. The generated x-rays are blocked by microstructures 700 to create an effective array of x-ray sub-sources. Microstructures 700 may be placed onto substrate portion 1004 and covered or encapsulated by substrate portion 1006. Alternatively, they may be formed by embedding the microstructures within a single substrate portion, as shown in target 1000 of FIG. 3C.

Figure 3C:
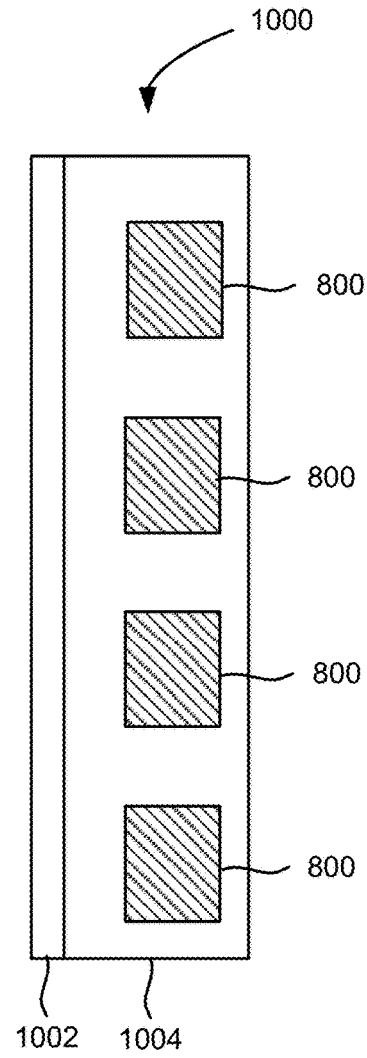
FIG. 3C illustrates an alternate substrate with an embedded target mask.

Though only one pattern of a microstructure element in target 1000 is illustrated in FIG. 3A-3C, other implementations are possible and considered within the scope of this disclosure. For example, target 1000 can include multiple target patterns formed by any combination of microstructures and masks, wherein one or more of the multiple target patterns can have multiple depths within a substrate.

Figure 3D:
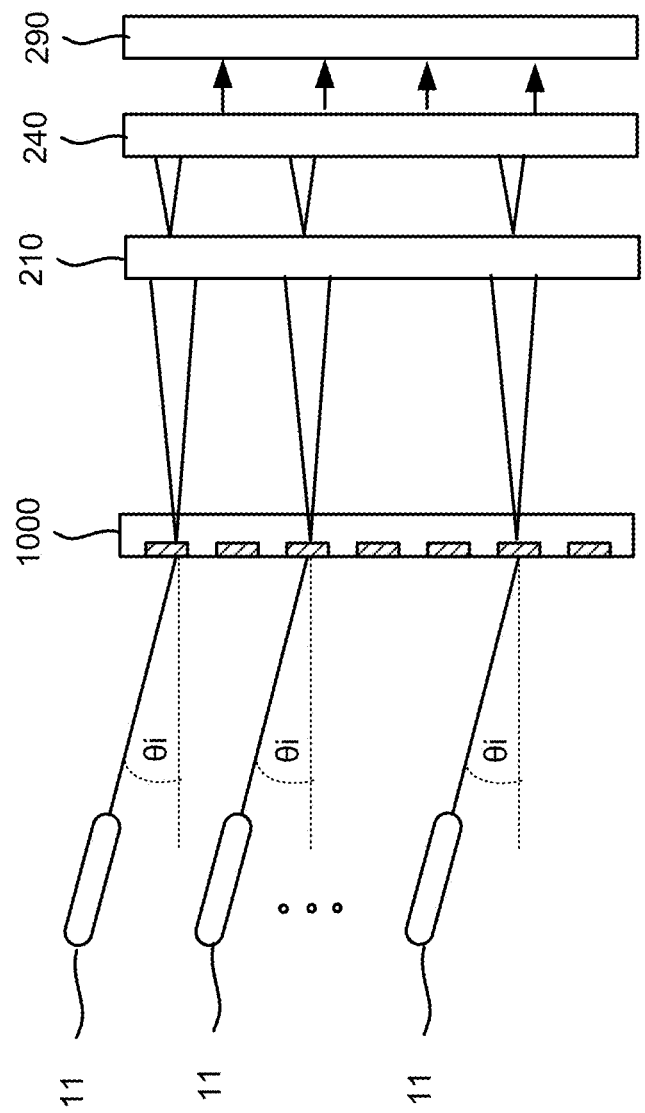
FIG. 3D illustrates a system having source electron beams bombarding a target at an oblique angle.

In some instances, the electron beam may be incident onto the target at an oblique angle. FIG. 3D illustrates a system having one or more electron beams 11 bombarding a target 1000 at an oblique angle, such as between 20 degrees and 80 degrees. In some instances, the incidence angle of the electron beams on the target may be about 60 degrees. Providing the incident electron beam at an oblique angle allows for a higher energy x-ray beam from the target and reduces scattering in substrates such as diamond.

Figure 3E:
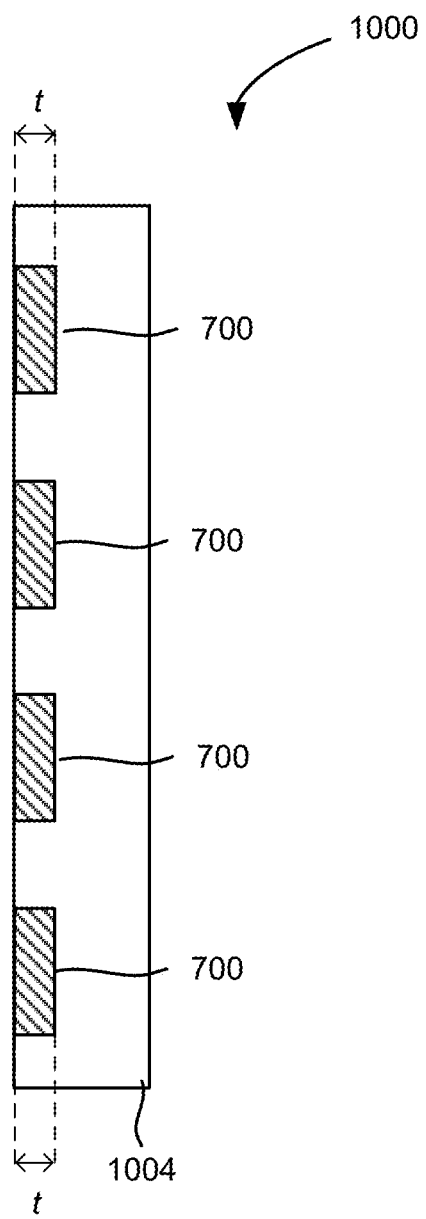
FIG. 3E illustrates a target having microstructures.
Figure 3F:
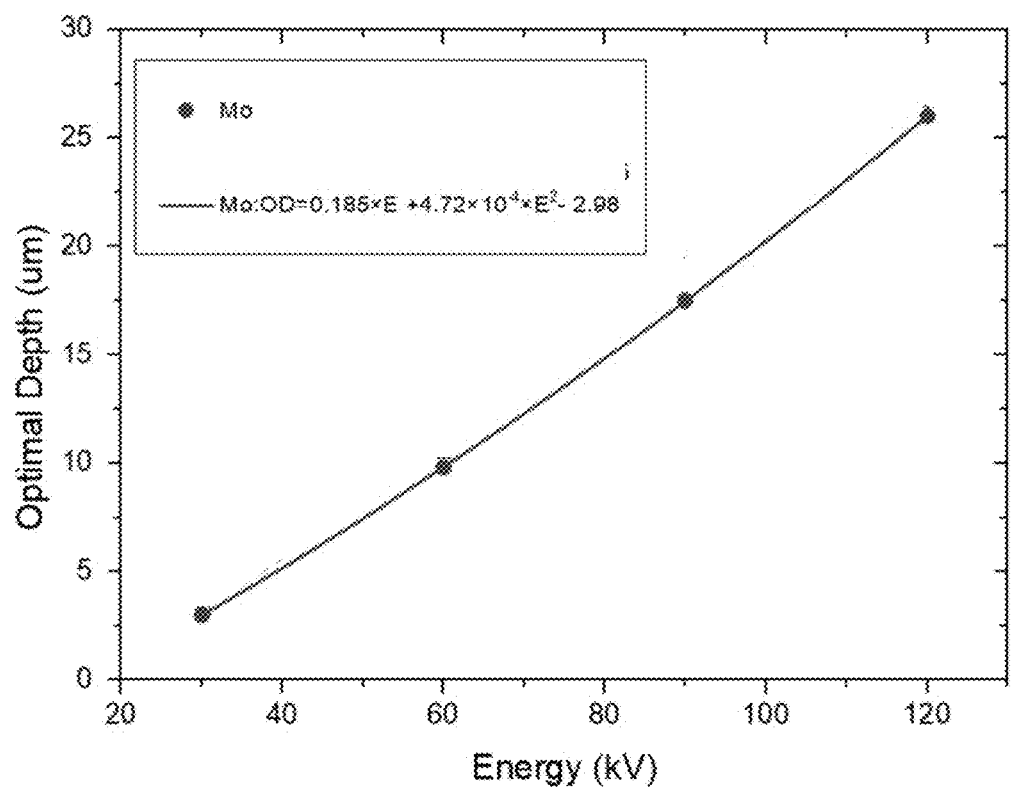
FIG. 3F illustrates a plot of optimal thickness vs. acceleration voltage for molybdenum.

FIG. 3E illustrates a target having a substrate 1004 (typically a low atomic material such as diamond) and microstructures 700. In some instances of the present technology, the thickness t of the targets can be optimized for the particular material to improve contrast between x-rays that are emitted the microstructures 700 and x-rays generated in the substrate. In some cases, the thicknesses are on the order of 2-10 um. In some instances, the depth of the target microstructure material within a substrate may be optimized to achieve a particular acceleration voltage. FIG. 3F illustrates a plot of optimal thickness vs. acceleration voltage for molybdenum (Mo) microstructures. As shown, the relationship between the optimal depth in micrometers to the acceleration voltage in kilovolts is approximately linear. For example, for an energy of 60 kV, the optimal depth would be about 10 microns. Though only data for molybdenum is displayed, the optimal depth of a target microstructure for other materials may also be optimized for a particular acceleration energy.

Some microstructured targets may furthermore comprise electrically conductive layers, layers to improve thermal conductivity between the microstructure and the substrate, and/or diffusion barriers.

1.3 X-Ray Source Filtering

In embodiments in which the micro-beams are generated by the Talbot effect, the bandwidth of the x-ray beams at the object to be examined must be within +/−15% of a predetermined x-ray energy of interest. This is typically achieved through the use of filters, such as thin metal foils.

2. Geometric Conditions

Returning to FIG. 3A, the x-rays 888 that emerge from the arrayed source as an array of individually spatially coherent but mutually incoherent sub-sources of illumination for the beam splitting grating $G_1$ 210-2D placed at a distance L from the arrayed x-ray source $A_0$. The position of the object 240-W to be illuminated by the array of micro-beams is placed at a further distance D from the beam-splitting grating $G_1$ 210-2D. To ensure that each x-ray sub-source in $A_0$ contributes constructively to the image-formation process, the geometry of the arrangement should satisfy the condition:

$$p_0 = p_2 \frac{L}{D} \qquad \text{[Eqn. 4]}$$

When the condition is met, the x-rays from the many sub-sources of $A_0$ produce the same (overlapping) Talbot interference pattern, and because the various mutually incoherent sources do not interfere with each other, these Talbot patterns will add as intensities. The effect at the object 240-W is therefore to simply increasing the intensity of the micro-beams (along with it the signal-to-noise ratio) above what a single coherent source can provide. This configuration is called the Talbot-Lau interferometer. It should be noted that the arrayed x-ray source may also be provided in some embodiments using a uniform x-ray material and a masked grating that allows x-rays to emerge only from specific points arranged in an array of dimension a and period $p_0$. An arrayed x-ray source may also be provided by selective bombardment of an x-ray generating material using a patterned electron beam.

The beam-splitting grating may be an amplitude grating with a 50/50 duty cycle, as illustrated in FIG. 3A, or may be an amplitude grating with some other duty cycle. A phase-shifting beam-splitting grating may comprise a 1-D or 2-D periodic pattern of n or π/2 phase-shifts.

To ensure that the object 240-W to be examined is illuminated by a periodic pattern of x-ray micro-beams, the distance D between the grating and the object should correspond to one of the fractional Talbot distances, i.e.

$$D = n\frac{2p_1^2}{16\lambda} \quad \text{[Eqn. 5]}$$

where n is a non-zero integer. The suitable value of n may be different if the grating is a transmission grating, a π phase-shifting grating, or a π/2 phase-shifting grating.

Another equation often used in Talbot-Lau systems relates the pitch $p_1$ of the Talbot grating $G_1$ to the size a of the x-ray generating elements in the arrayed source:

$$p_1 \geq L\frac{\lambda}{a} \quad \text{[Eqn. 6]}$$

Most embodiments of the invention employ a interferometric system in which the conditions presented in Eqns. 4-6 are met.

In some embodiments, the object 240-W to be examined may be mounted on a position controller 245 that may be controlled to translate the object 240-W in x- and y-dimensions. For some embodiments, additional rotation of the object for generating tomographic imaging data may also be controlled by the mounting system. In some embodiments, a 5-axis mount, or a goniometer, may be used.

It should be noted that these embodiments as illustrated are not to scale.

3. Detector Considerations

As disclosed here, the detector pitch will be matched to the pitch of the multiple microbeams so that each pixel is positioned to only detect x-rays emerging from the interaction of the object with a single micro-beam, and the cross-talk between pixels due to neighboring micro-beams is minimized. Then, the data collection and final reconstruction of the "map" of the properties of the object may proceed, knowing that the distinct signals from each pixel need not be further deconvolved. If there is cross-talk between micro-beams and pixels (e.g. due to scattering or fluorescence), additional image analysis may be able to remove some of the cross-talk if it can be properly calibrated. Energy resolving array detectors may also be used to separate signals from transmitted x-rays, scattered x-rays, and fluorescence x-rays.

This matching is most straightforwardly achieved if the detector pitch is a 1:1 match to the pitch of the micro-beams, i.e. each beam has a corresponding single pixel in the detector, and the detector is placed in close proximity to the object and the micro-beams.

3.1 Finer Detector Pitch

In some embodiments, detector pitches that are integer fractions of the pitch of the micro-beams (e.g. a 2× reduction in pitch, which would indicate, for example, in a 2-D array, that 4 pixels are positioned to collect the x-rays corresponding to a single micro-beam, or a 3× reduction in pitch, which would indicate 9 pixels are present to detect the x-rays corresponding to each micro-beam) may also be used. This may offer some advantages if the x-rays being detected have some spatial structure, for example if the desired x-ray signal is related to small-angle scattering from the object. Then, certain pixels of the detector can be aligned to detect only the scattered x-rays, while the non-scattered beam may be collected by a different pixel, or simply blocked.

3.2. Larger Detector Pitch.

In other embodiments, a larger detector pixel may be used. In this case, a pixel size that is larger than the pitch of the Talbot fringe may be used, as long as the active area of each pixel of the detector (the portion converting x-rays into an electronic signal) is on the order of the same size as the corresponding x-ray micro-beam. The detector may therefore be less expensive, and yet still produce a "high resolution" signal (since the spatial resolution is determined by the interaction volume of the Talbot fringe and the object, not the detector pixel size).

One disadvantage of this technique is that only 1 out of 4 Talbot fringes is used for detection, and the other fringes are wasted. Although certain Talbot fringes will end up not being used, the missing information may still be provided by scanning over the distance between detector pixel centers. And furthermore, with a larger pixel, greater detection efficiency may be achieved for the micro-beams that are detected.

Figure 5:
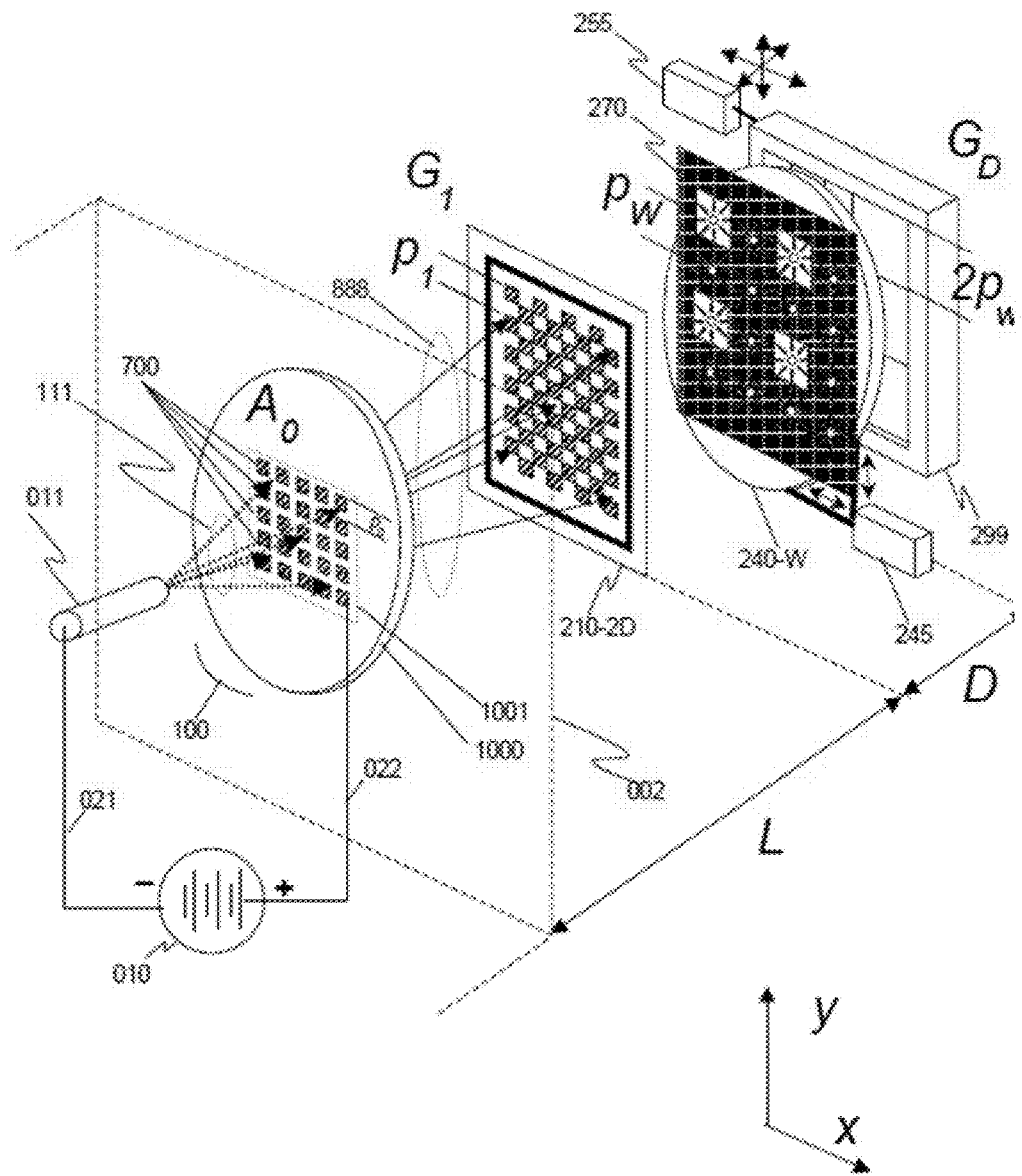
FIG. 5 illustrates a schematic view of a microscope according to an embodiment of the invention having a mask placed in front of the object under examination.

FIGS. 5-12 illustrate the use of larger pixels in some embodiments of the invention. FIG. 5 illustrates a schematic of an embodiment of a system similar to that of FIG. 3A, but in which a mask has been placed in front of the object 240-W to block a certain number of micro-beams. As illustrated, 3 out of every 4 micro-beams are blocked, with only 1 beam out of 4 proceeding to illuminate the object and then be detected by the detector, but any number of beams may be blocked according to predetermined patterns for various applications.

Figure 6A:
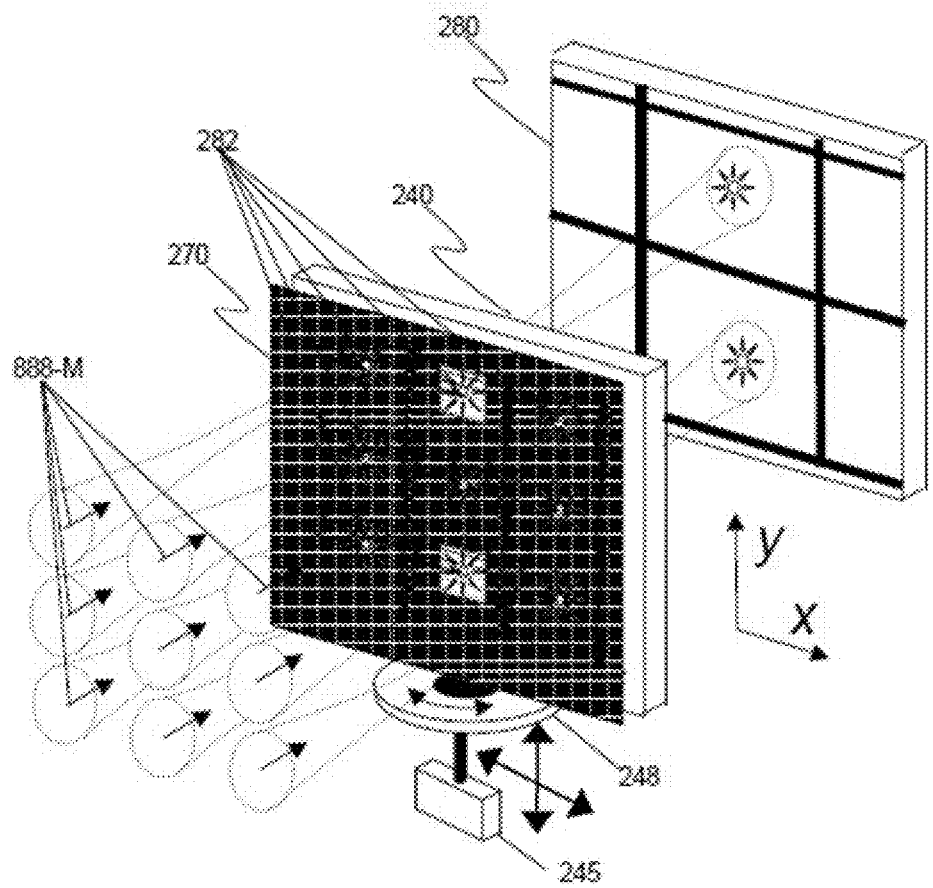
FIG. 6A illustrates a schematic view of the micro-beams, object, and detector of the embodiment of FIG. 5.
Figure 6B:
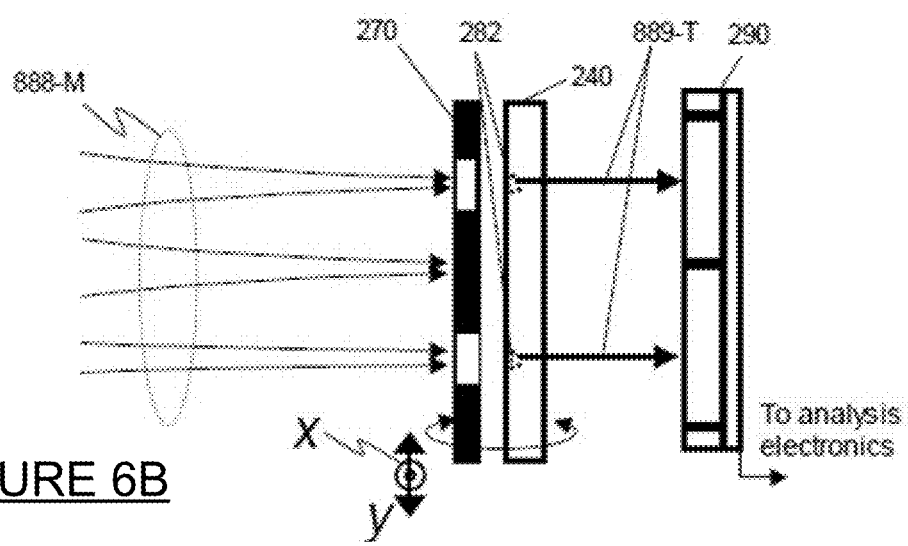
FIG. 6B illustrates a schematic cross-section view of the micro-beams, object, and detector of the embodiment of FIG. 5.

FIGS. 6A and 6B illustrate such an embodiment in more detail, presenting illustrations similar to those of FIGS. 4A and 4B. As can be seen by the comparison with FIGS. 4A and 4B, because only a certain number of micro-beams are used, the pitch of beams at the detector is substantially larger, and a less expensive detector with a larger pixel size may be used.

As illustrated in FIGS. 3 through 6B, the x-ray detector is presented as a direct array detector, generating an electrical signal in response to the absorption of x-rays. Such an electronic sensor may directly create an electrical signal in response to the absorption of x-rays, by, for example, the creation of direct electron-hole pairs in amorphous selenium (a-Se). These are then converted into electronic signals using an array of thin-film transistors (TFTs). Such direct flat panel detectors (FPDs) such as the Safire FPD of Shimadzu Corp. of Kyoto, Japan, are commercially available.

In other embodiments, the detector may use scintillators that emit visible or ultraviolet light when exposed to x-rays. The active x-ray detection region may be defined, for example, by providing a scintillator such as cesium iodide doped with thallium (CsI(Tl)) or by providing a detector with a uniform coating of scintillator with a masking layer of high Z material, for example, gold (Au), on top.

Figure 7:
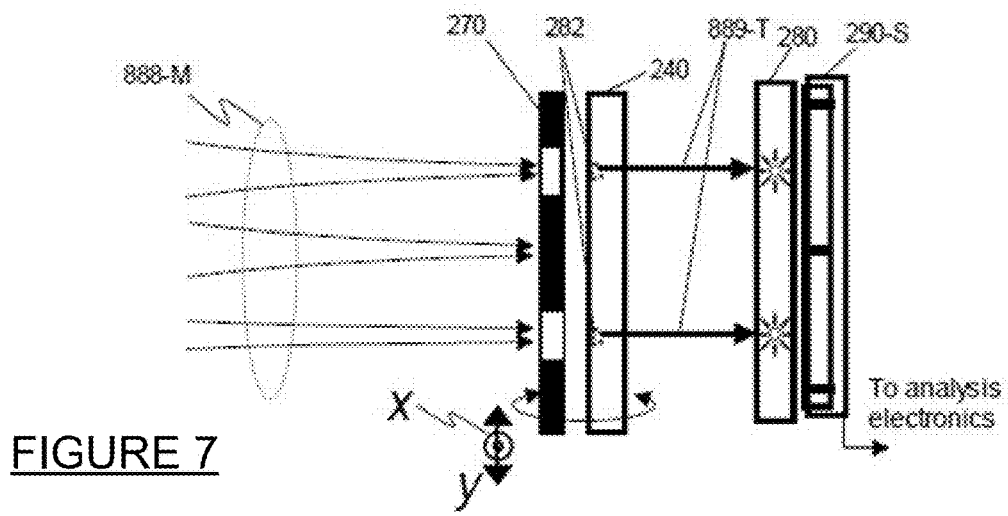
FIG. 7 illustrates a schematic cross-section view of the micro-beams, object, and detector of an embodiment comprising a scintillator.

FIG. 7 illustrates a variation of the embodiment of FIG. 6B, but using a detector 290-S in combination with a fluorescent screen or scintillator 280. The scintillator 280 comprises a material that emits visible and/or UV photons when x-rays are absorbed, and the detector 290-S detects those visible and/or UV photons. Typical scintillator materials comprise a layer of cesium iodide (CsI), thallium doped CsI, yttrium aluminium garnet (YAG) or gadolinium sulfoxylate (GOS).

In conventional imaging systems, high resolution images with a scintillator-type detector in close proximity to the object can be obtained, but the overall thickness of the scintillator and electronic elements must be thin enough so that each detector pixel is collecting only x-rays corresponding to that pixel.

However, in the system disclosed herein, the spatial resolution is defined by the dimensions of the micro-beams 888-M instead of the detector pixel size. This allows a larger pixel and thereby a thicker scintillator material to be used, since every photon generated from the larger pixel will be known to have originated from a predetermined microbeam. The thicker scintillator increases the probability that a given x-ray photon will be absorbed and converted to visible light, increasing the potential signal.

Some additional number of x-ray photons will generate secondary electrons in the scintillator material, which may in turn excite additional visible/UV emission from the scintillator material. However, as all x-ray photons within the pixel are known to have originated from a single micro-beam, the additional photons emerging from this excitation are also known to have their origin with these spatially defined x-rays, and simply increase the overall signal that may be detected.

Figure 8:
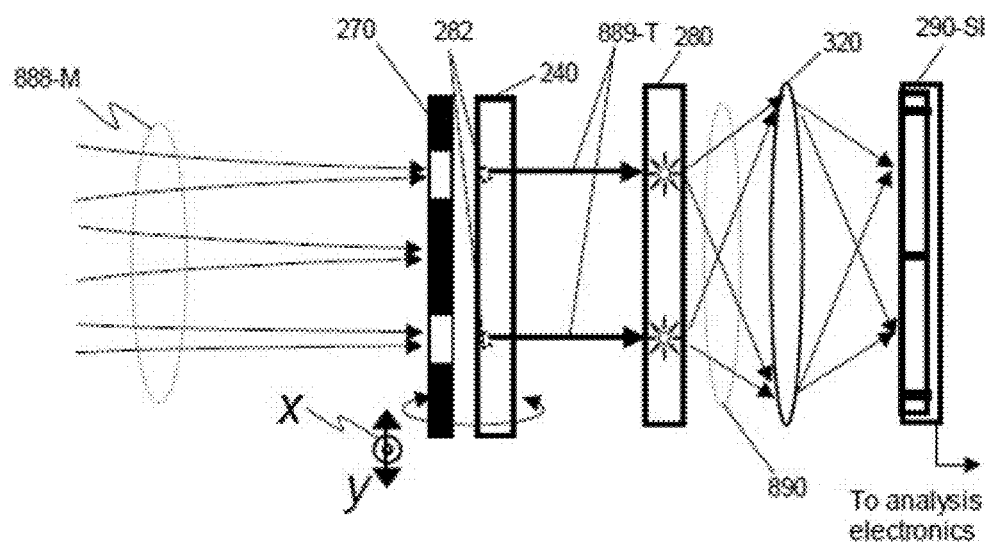
FIG. 8 illustrates a schematic cross-section view of the micro-beams, object, and detector of an embodiment comprising a scintillator and a scintillator imaging system.

FIG. 8 illustrates an additional variation on a system using a scintillator, in which the visible/UV light 890 from the scintillator 280 is collected by a visible/UV optical system 320 and imaged onto a detector 290-SI. The visible/UV optical system may comprise optics with additionally magnify the image of the scintillator. When using relay optics and a magnified image, the electronic detector need not comprise a high resolution sensor itself, and less expensive commercial CCD detectors or complementary metal-oxide-semiconductor (CMOS) sensor arrays with, for example, 1024×1024 pixels, each 24 μm×24 μm square, may be used.

Thicker scintillators may also be used in some embodiments having relay optics, increasing sensitivity. However, when relay optics are used, detection is limited to the field of view collected by the x-ray optics, which may in some cases be only on the order of hundreds of microns. Collecting data on larger areas will then need to be "stitched" together from several exposures.

Figure 9:
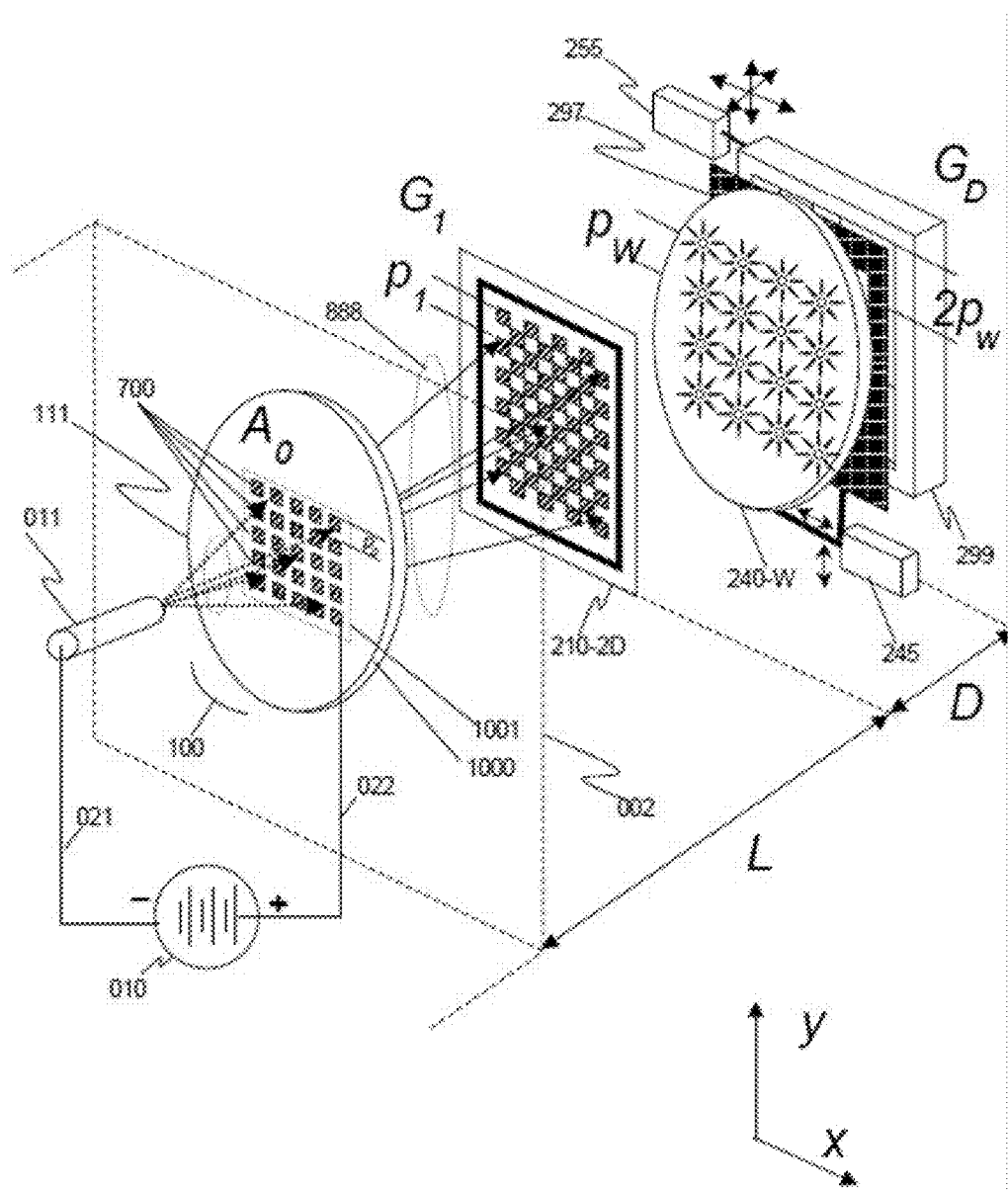
FIG. 9 illustrates a schematic view of a microscope according to an embodiment of the invention having a mask placed in front of the object under examination.
Figure 10A:
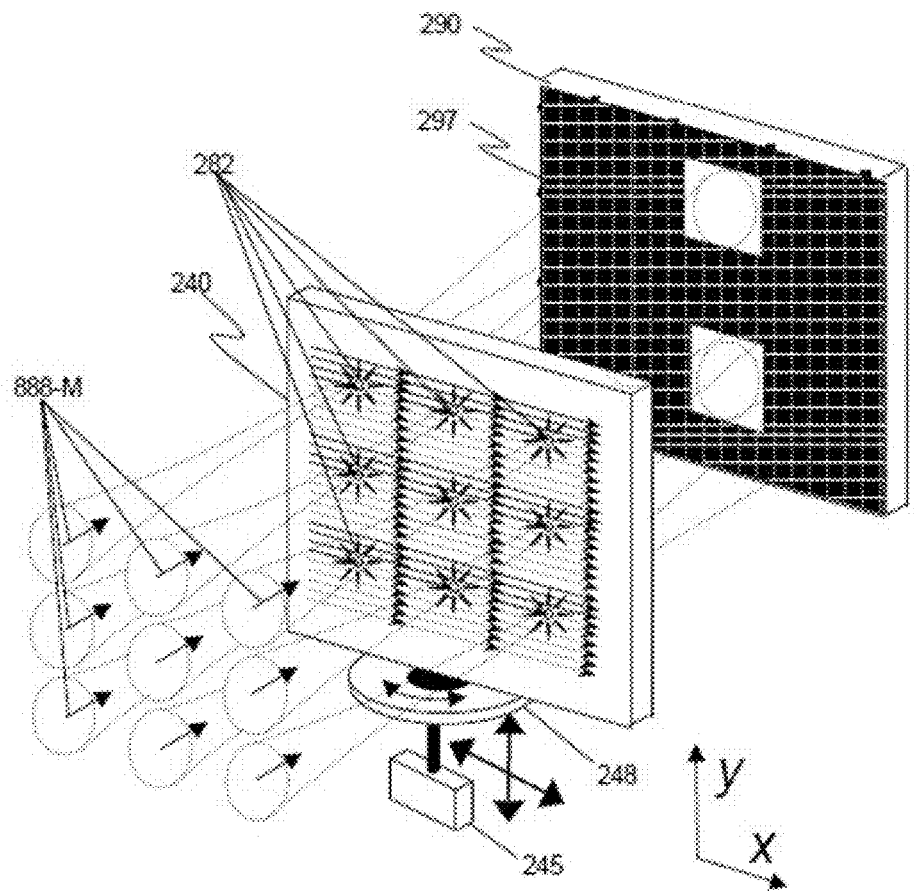
FIG. 10A illustrates a schematic view of the micro-beams, object, and detector of the embodiment of FIG. 5.
Figure 10B:
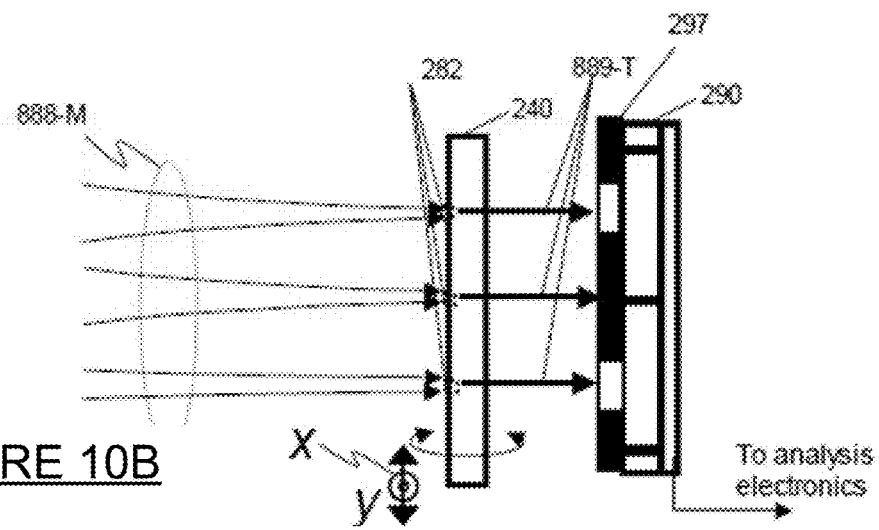
FIG. 10B illustrates a schematic cross-section view of the micro-beams, object, and detector of the embodiment of FIG. 5.

FIGS. 9, 10A and 10B represent an additional embodiment in which a masking structure 297 is placed between the object 240 and the detector. For this embodiment, all available micro-beams 888-M illuminate the object 240, but a masking layer 297 made of, for example, gold (Au), prevents 3 out of every 4 beams from entering the detector 290. This also allows detector 290 to have a larger pixel, again reducing cost for direct detectors and, for embodiments using scintillators, increasing potential detector efficiency.

Figure 11:
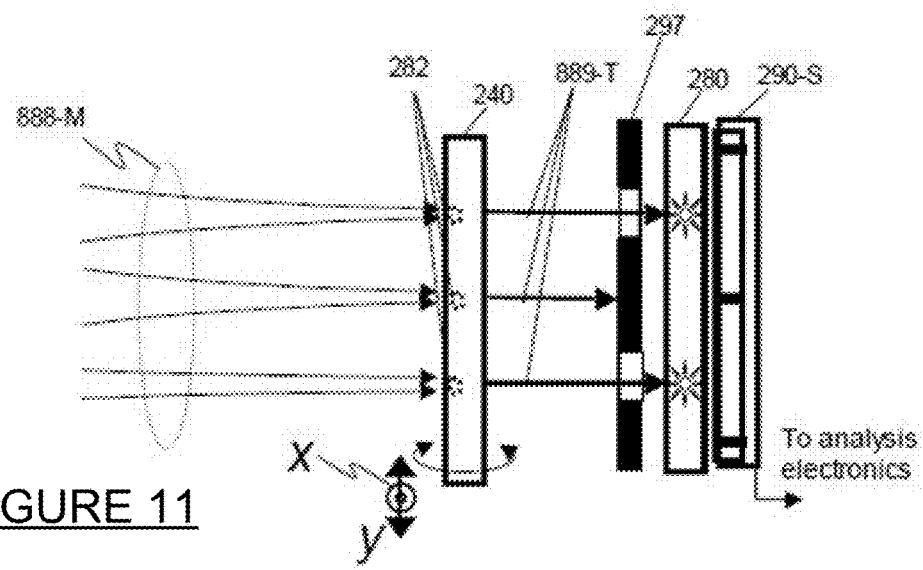
FIG. 11 illustrates a schematic cross-section view of the micro-beams, object, and detector of an embodiment comprising a mask at the detector and a scintillator.

FIG. 11 illustrates an additional variation of the embodiment of FIGS. 9, 10A and 10B, but with the detection of x-rays achieved using a scintillator 280 and a visible/UV detector 290-S.

Figure 12:
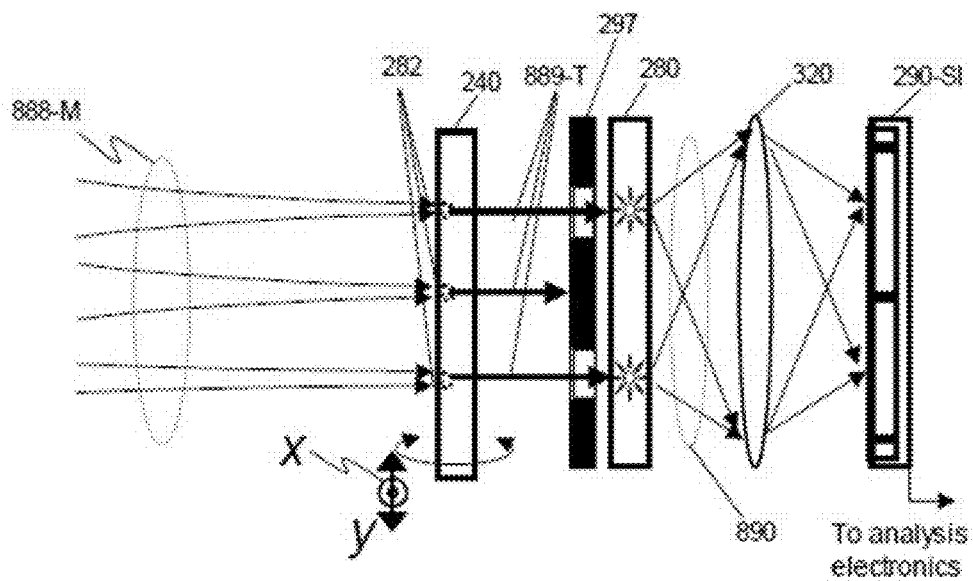
FIG. 12 illustrates a schematic cross-section view of the micro-beams, object, and detector of an embodiment comprising a mask at the detector and a scintillator and a scintillator imaging system.

FIG. 12 illustrates an additional variation on a system using a scintillator, in which the visible/UV light 890 from the scintillator 280 is collected by a visible/UV optical system 320 and imaged onto a detector 290-SI.

Although the scintillators as illustrated in FIGS. 7, 8, 11, and 12 are shown as comprising uniform layers of scintillator, embodiments using patterned scintillator material, in which scintillator material is placed only over a portion of the pixel, may also be used. The selective placement of scintillator material over portions of the detector may be used as an alternative to the use of a masking layer to select certain micro-beams for detection.

Detectors with additional structure within each pixel may also be employed as well. For example, if the typical detector pixel is 2.5 microns by 2.5 microns (an area of 6.25 micron$^2$), but the micro-beam diameter is only 1 micron, a detector pixel with a central "spot" of scintillator material slightly larger than 1 micron, surrounded by "dead" zones, and positioned to correspond to the position of the microbeam may be created. With this configuration, all the x-rays from the micro-beam should be detected, while reducing the detection of scattered or diffracted x-rays that would otherwise cause spurious signals if the full area of the detector pixel were to be used.

Likewise, pixels in which detector structures (such as scintillator material) are only positioned on the outer portion of the pixel, for example, to only detect x-rays scattered at small angles while not detecting the directly transmitted beam, may also be used for some embodiments.

Likewise, although the mask 297 in FIGS. 11 and 12 is shown as displaced from the scintillator layer, some embodiments may have the masking layer directly deposited onto the scintillator layer. Other embodiments for patterned scintillators may be known to those skilled in the art.

3.0 Methods of Microscopic Data Gathering.

Figure 13:
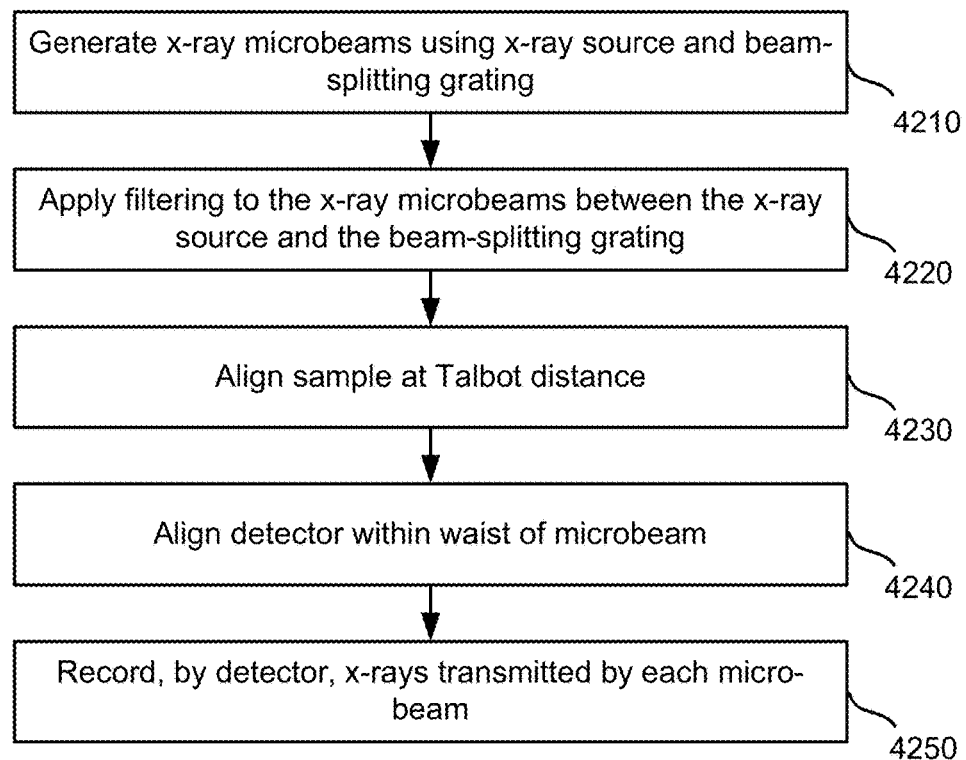
FIG. 13 illustrates a method for collecting microscopy data.

FIG. 13 illustrates method for collecting microscopy data. The data collection may be used to form a 2-D "map" or 3-D tomographic image.

X-ray microbeams are generated in step 4210 through the use of an x-ray source and a beam-splitting grating, preferably a phase grating. In some instances, the x-ray source employs an x-ray target comprised of microstructures on or embedded within a substrate of low mass density (e.g. diamond or Be). In some instances, the x-ray source employs a target comprising a thin film coated on top of a substrate of low mass density and furthermore comprising embedded microstructures that serve as a "mask" to block a portion of the x-ray beams. In some instances, the x-ray source is an extended x-ray source and is used in combination with an absorbing grating. In some instances, the x-ray source is a microfocus x-ray source.

A filtering method is placed 4220 between the x-ray source and the beam-splitting grating to limit the bandwidth of the x-rays from the x-ray source to a bandwidth. In some instances, the bandwidth of the illumination beam can be ±15%, depending on which pre-determined Talbot or fractional Talbot distance is used.

An object to be examined is aligned 4230 at a Talbot distance such that the region of nodes (darkest intensity) and anti-nodes (highest intensity) of the microbeam has a pitch p in the directions orthogonal to the propagation direction (designated the "x" and "y" directions) is 20 micrometers or less. The contrast between regions of greatest intensity (generally at the center of the micro-beams) and the darkest intensity (generally the region exactly between microbeams) is preferred to be at least 20%, although in some cases, an intensity ratio of 1.2:1 or 2:1 between the anti-nodes and nodes may provide enough contrast. In some instances, the bandwidth of the illumination beam satisfies the following equation:

$$\Delta\lambda = \frac{\lambda_0}{2m-1}.$$

A detector is aligned 4240 within the "waist" of the microbeams so that each detector pixel generates signals corresponding to a single microbeam. For the micro-beams formed by an imaging system, this position may correspond to the depth-of-focus of the imaging system. In most instances, the detector pixel pitch and microbeam are the same or approximate with some scaling, such that the center of each microbeam is coincident upon the center of the detector pixel.

For micro-beams formed by a Talbot system, this may correspond to the position of the interference pattern at a fractional or integer multiple of the Talbot Distance, where self-replicating images are formed. There is some flexibility in the exact positioning of the detector, as long as each pixel of the detector generates a signal corresponding only to a single micro-beam (without cross-talk between the micro-beams or detector pixels). Generally, a detector will be chosen where every micro-beam has a corresponding pixel or set of pixels; however, in some embodiments, the detector may only detect a subset of the micro-beams. In some instances, a detector can be chosen to having a pixel pitch pd equal to a non-zero integer multiple of the micro-beam pitch p.

X-rays transmitted by each microbeam are recorded 4250 by the detector, and the corresponding electronic signals representing x-ray intensity and energy are recorded.

If only a single set of datapoints are desired, no more data need be collected. In most embodiments, however, the object to be examined is moved 4260 using a position controller to build up a 1-D or 2-D "map" of the properties of the object. This is typically performed so that the object is moved several times corresponding to to the FWHM of each microbeam region of highest intensity and moved in both x and y dimensions.

If no information beyond a 2-D scan in x- and/or y-dimensions is needed, the present system can take the accumulated data and, in this case, use various image "stitching" techniques that are generally well known in the art, synthesize a 2-D intensity "map" representing the large-area x-ray transmission/absorption of the object.

If, on the other hand, 3-D information is desired, the object is rotated through an angle relative to the z-axis (this rotation may be a rotation around either the x- or y-dimensions) to collect a set of data from the x-ray detector at this alternative rotation position. The system will loop through these steps to collect x-ray information at a preprogrammed sequence of positions and rotations until a complete set of data is collected. At this point, the system will then proceed to take the accumulated data and, in this case, use various image 3-D analysis techniques that are generally well known in the art, to synthesize a 3-D representation of the large-area x-ray transmission/absorption of the object.

Variations on the method described above may also be put into practice. For example, instead of first executing a loop of data collection in x- and y-dimensions at a fixed rotation position, and then changing the rotation setting to collect additional data, embodiments in which the object is rotated by a mechanical mechanism while the x- and y-position settings remain fixed may also be executed. Rotation of the object around the z-axis may also provide additional information that can be used in image tomosynthesis.

4. Limitations and Extensions.

With this Application, several embodiments of the invention, including the best mode contemplated by the inventors, have been disclosed. It will be recognized that, while specific embodiments may be presented, elements discussed in detail only for some embodiments may also be applied to others. Also, details and various elements described as being in the prior art may also be applied to various embodiments of the invention. While specific materials, designs, configurations and fabrication steps have been set forth to describe this invention and the preferred embodiments, such descriptions are not intended to be limiting. Modifications and changes may be apparent to those skilled in the art, and it is intended that this invention be limited only by the scope of the appended claims.

What is claimed is:

1. An x-ray microscope system comprising:
   an x-ray illumination beam generating system comprising:
      an x-ray source; and
      a beam-splitting grating, wherein said x-ray illumination beam generating system produces a plurality of x-ray micro-beams through the Talbot effect, the plurality of x-ray micro-beams having a depth-of-focus, an axis of propagation and a predetermined intensity profile normal to said axis for a predetermined x-ray energy;
   a mount configured to support an object to be examined within the depth-of-focus, the mount configured to move the object relative to said plurality of x-ray micro-beams; and
   at least one x-ray pixel array detector for detecting x-rays resulting from interaction of said plurality of x-ray micro-beams with said object, said detector comprising a plurality of pixels within said depth-of-focus.

2. The x-ray microscope system of claim 1, wherein the beam-splitting grating is a $\pi$ phase-shifting grating or a $\pi/2$ phase-shifting grating at said predetermined x-ray energy.

3. The x-ray microscope system of claim 1, wherein the x-ray source comprises:
   an emitter for an electron beam; and
   a transmission x-ray target comprising a plurality of discrete microstructures comprising a first material having a first mass density and a substrate comprising a second material having a second mass density lower than the first mass density.

4. The x-ray microscope system of claim 3, wherein the energy of the electron beam is greater than 1.1 times of the predetermined x-ray energy.

5. The x-ray microscope system of claim 3, wherein the electron beam is incident upon the target at an oblique angle.

6. The x-ray microscope system of claim 1, wherein the x-ray source is a microfocus x-ray source or an extended x-ray source used in combination with an absorption grating.

7. The x-ray microscope system of claim 1, further comprising at least one filter so that the full width half maximum of the bandwidth of the plurality of x-ray micro-beams is 30% centered at the predetermined x-ray energy.

8. The x-ray microscope system of claim 1, wherein the mount is configured to translate the object in two orthogonal directions.

9. The x-ray microscope system of claim 8, wherein the mount is further configured to rotate the object about a direction perpendicular to the axis of propagation.

10. The x-ray microscope system of claim 1, wherein the detector is a CCD-based detector and is aligned such that centers of the pixels are aligned to centers of the x-ray micro-beams.

11. The x-ray microscope system of claim 1, further comprising an analysis system configured to display and analyze output signals from the detector.

12. The x-ray microscope system of claim 1, further comprising a mask positioned to block a predetermined number of the x-ray micro-beams.

13. The x-ray microscope system of claim 1, further comprising a mask positioned upstream of the detector to block a predetermined number of the x-ray micro-beams transmitted through the object.

14. The x-ray microscope system of claim 1, in which the system achieves submicron spatial resolution.

15. The x-ray microscope system of claim 1, wherein each pixel comprises an actively detecting area at a center of the pixel, the actively detecting area comprising less than 50% of a total area of the pixel.

16. The x-ray microscope system of claim 1, further comprising an attenuating grating placed upstream of the detector and positioned to absorb x-rays between the x-ray micro-beams to increase the intensity ratio between x-ray micro-beams and the regions between the x-ray micro-beams.

17. A method for measuring the x-ray transmission of an object, the method comprising:
    producing an x-ray Talbot interference pattern comprising a plurality of anti-nodes and having a depth-of-focus;
    positioning an x-ray array detector comprising a plurality of pixels such that the plurality of pixels are within the depth-of-focus of the x-ray Talbot interference pattern; and
    positioning an object to be examined within the depth-of-focus such that x-rays of at least some of the anti-nodes transmitted through the object to be examined are detected by the detector.

18. The method of claim 17, further comprising blocking at least some of the x-rays transmitted through the object from being detected by the detector.

19. The method of claim 17, further comprising blocking at least some x-rays of the x-ray Talbot interference pattern from reaching the object.

20. The method of claim 19, wherein said blocking comprises positioning a mask in front of the object.

21. The method of claim 20, wherein the mask is positioned within the depth-of-focus.

\* \* \* \* \*